US007770738B2

United States Patent
Tabata et al.

(10) Patent No.: US 7,770,738 B2
(45) Date of Patent: Aug. 10, 2010

(54) CLASSIFYING DEVICE AND METHOD OF CLASSIFICATION

(75) Inventors: Kazuaki Tabata, Kanagawa (JP);
Hiroshi Kojima, Kanagawa (JP);
Kazuya Hongo, Kanagawa (JP);
Takayuki Yamada, Kanagawa (JP);
Seiichi Takagi, Kanagawa (JP); Tetsuo Ohta, Kanagawa (JP); Masaki Hirota, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 0 days.

(21) Appl. No.: 12/391,694

(22) Filed: Feb. 24, 2009

(65) Prior Publication Data
US 2010/0072116 A1  Mar. 25, 2010

(30) Foreign Application Priority Data
Sep. 25, 2008  (JP) .............................. 2008-246973

(51) Int. Cl.
*B07B 13/00* (2006.01)
*B07C 5/12* (2006.01)
(52) U.S. Cl. .......................... 209/680; 209/13; 209/279; 209/350; 209/725; 209/731; 210/359; 210/459; 210/460; 210/512.1; 210/781
(58) Field of Classification Search ................... 209/13, 209/279, 350, 680, 725, 731–734; 210/359, 210/459, 460, 512.1, 512.2, 781, 787
See application file for complete search history.

(56) References Cited

U.S. PATENT DOCUMENTS 5,454,472 A * 10/1995 Benecke et al. .......... 209/127.1

(Continued)

FOREIGN PATENT DOCUMENTS

JP   A-2007-268491   10/2007

(Continued)

OTHER PUBLICATIONS

Ji et al., "A Centrifugation-Enhanced High-Efficiency Micro-Filter with Spiral Channel," IEEE Transducers and Eurosensors (The 14th International Conference on Solid-State Sensors, Actuators and Microsystems), 2007, pp. 1865-1868.

(Continued)

*Primary Examiner*—Gene Crawford
*Assistant Examiner*—Terrell H Matthews
(74) *Attorney, Agent, or Firm*—Oliff & Berridge, PLC

(57) ABSTRACT

A classifying device for classifying particles using a centrifugal force contains a microchannel includes a curved portion including a first tubular channel and a second tubular channel; and a diaphragm that is provided within the curved portion, and that is located at a position between the first tubular channel and the second tubular channel; and wherein the diaphragm has at least a first apertured group formed in a central region of the diaphragm and a second apertured group formed in a first end region and a second end region of the diaphragm, the first apertured group and the second apertured group communicate the first tubular channel with the second tubular channel along a direction of the centrifugal force, the first apertured group has a mesh, and the second apertured group has a mesh that is different in size from the mesh of the first apertured group.

19 Claims, 20 Drawing Sheets

U.S. PATENT DOCUMENTS

| | | | |
|---|---|---|---|
| 6,739,456 B2 * | 5/2004 | Svoronos et al. | 209/725 |
| 7,472,794 B2 * | 1/2009 | Oakey et al. | 210/420 |
| 2002/0053532 A1 * | 5/2002 | Quake et al. | 209/2 |
| 2008/0128331 A1 * | 6/2008 | Lean et al. | 209/155 |

OTHER PUBLICATIONS

Wang et al., Microfluidic Centrifugation in a Spiral Microchannel, the 10$^{th}$ International Conference on Miniaturized Systems for Chemistry and Life Sciences (μTAS2006), 2006, pp. 543-545.

* cited by examiner $r(\mu m) = 35\theta(rad) + 100$

REMOVAL OF FINE PARTICLES (CUTOFF PARTICLE SIZE: 10 μm)

ns of Samples $S_1$, $T_1$ and $T_2$ in each of Example 1 and Comparative Example 1;

CLASSIFYING DEVICE AND METHOD OF CLASSIFICATION

CROSS-REFERENCE TO RELATED APPLICATIONS

This application is based on and claims priority under 35 U.S.C. 119 from Japanese Patent Application No. 2008-246973 filed on Sep. 25, 2008.

BACKGROUND

1. Technical Field

The present invention relates to a classifying device and a method of classification.

2. Related Art

Methods of classifying particles by utilizing centrifugal force exerted on fluid which flows through a microchannel formed in the shape of a spiral have been put forth. These methods cause no clogging and ensure high durability in contrast to filter classification.

In addition, there is a proposal of a micro device which has a microchannel for allowing reaction of a reactant fluid containing a catalyst and is characterized in that the microchannel has a curved portion.

SUMMARY

According to an aspect of the present invention, there is provided a classifying device for classifying particles using a centrifugal force, the classifying device comprising:

A classifying device for classifying particles using a centrifugal force, the classifying device containing:

a microchannel that includes a curved portion including a first tubular channel and a second tubular channel; and a diaphragm that is provided within the curved portion, and that is located at a position between the first tubular channel and the second tubular channel; and wherein the diaphragm has at least a first apertured group formed in a central region of the diaphragm and a second apertured group formed in a first end region and a second end region of the diaphragm, the central region being sandwiched between the first end region and the second end region, the first apertured group and the second apertured group communicate the first tubular channel with the second tubular channel along a direction of the centrifugal force, the first apertured group has a mesh, and the second apertured group has a mesh that is different in size from the mesh of the first apertured group.

BRIEF DESCRIPTION OF THE DRAWINGS

Exemplary embodiment of the present invention will be described in detail based on the following figures, wherein.

DETAILED DESCRIPTION

Figure 1:
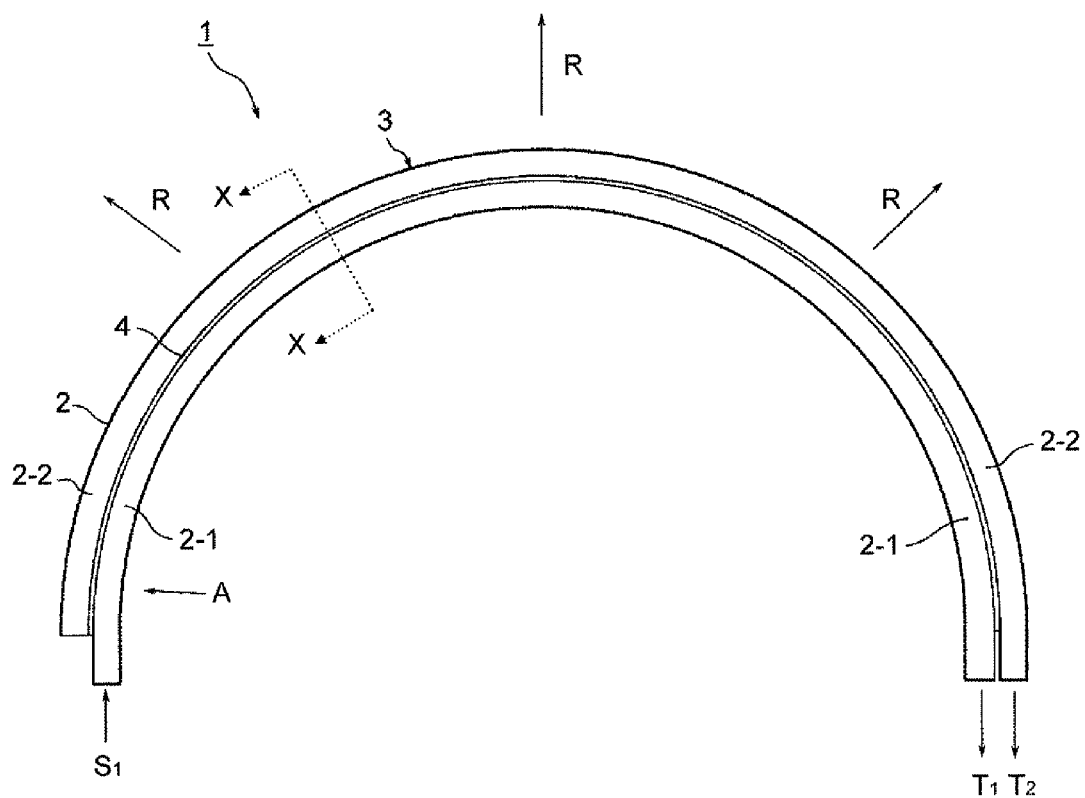
FIG. 1 is a top view of one example of the classifying device as an exemplary embodiment of the invention.

The classifying device as an exemplary embodiment of the invention has a microchannel having a curved portion and is characterized in that the curved portion incorporates a diaphragm which has at least two apertured groups which have different meshes and face toward centrifugal force. A mesh of apertured group formed in a central region of the diaphragm in the vertical direction differs in size from mesh of apertured group formed in regions located near the channel's bottom face and top face (end regions) of the diaphragm. The curved portion is partitioned into two channels, namely inner and outer channels, with the diaphragm.

The method of classifying particles in accordance with an exemplary embodiment of the invention is characterized by having a process in which a particles-dispersed liquid is fed into one of the two channels into which the curved portion is partitioned with the diaphragm in the classifying device as an exemplary embodiment of the invention.

These embodiments of the invention are described below in detail while referring to drawings as appropriate. Incidentally, when some objects are represented by one and the same symbol in the following description, they are identical with one another unless otherwise indicated.

(Microchannel)

The classifying device as an exemplary embodiment of the invention has a microchannel having a curved portion.

As the microchannel, a channel in several µm to several thousand µm width (circle-equivalent channel diameter) is preferably used. The classifying device as an exemplary embodiment of the invention is preferably a device having at least two micro-scale channels.

In the classifying device as an exemplary embodiment of the invention, the microchannel is on a micro scale, so it is small in both size and flow velocity and the Reynolds number thereof is 2,300 or below. Therefore, the classifying device having micro-scale channels is a device under the domination of a laminar flow but not a turbulent flow which dominates in usual reaction devices.

Herein, the Reynolds number (Re) is expressed in the following relation, and the laminar-flow domination is achieved when Re is 2,300 or lower.

$Re=uL/v$ (u: flow velocity, L: typical length, v: coefficient of kinematic viscosity)

In an exemplary embodiment of the invention, the equivalent diameter of the microchannel (circle-equivalent channel diameter) is preferably 5 mm or smaller, far preferably 1 mm or smaller, further preferably 0.8 mm or smaller, particularly preferably 0.5 mm or smaller.

In an exemplary embodiment of the invention, the microchannel has no particular restrictions so long as it has at least one curved portion. The curved portion preferably has a curved shape, but it may be bent into the shape of a non-curved line (e.g., a rectangular shape). Alternatively, the curved portion may have an elliptical or semicircular shape.

Additionally, centrifugal force is generated in the curved portion. The centrifugal force has a direction that moves away from the rotation axis (the center of the curved portion) The direction of centrifugal force in an exemplary embodiment of the invention is a direction that moves away from the rotation axis.

Figure 2:
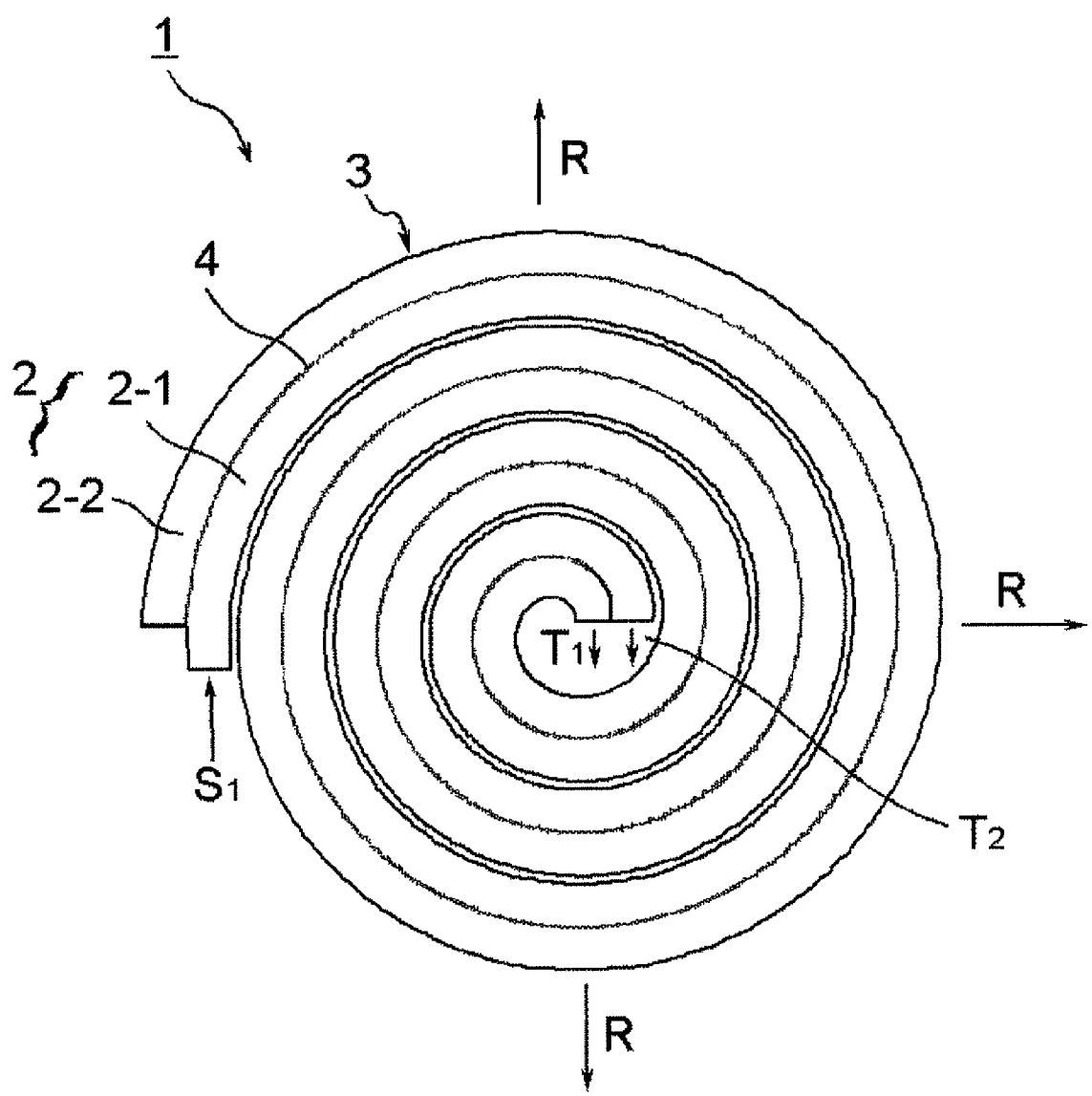
FIG. 2 is a top view of another example of the classifying device as an exemplary embodiment of the invention.
Figure 3:
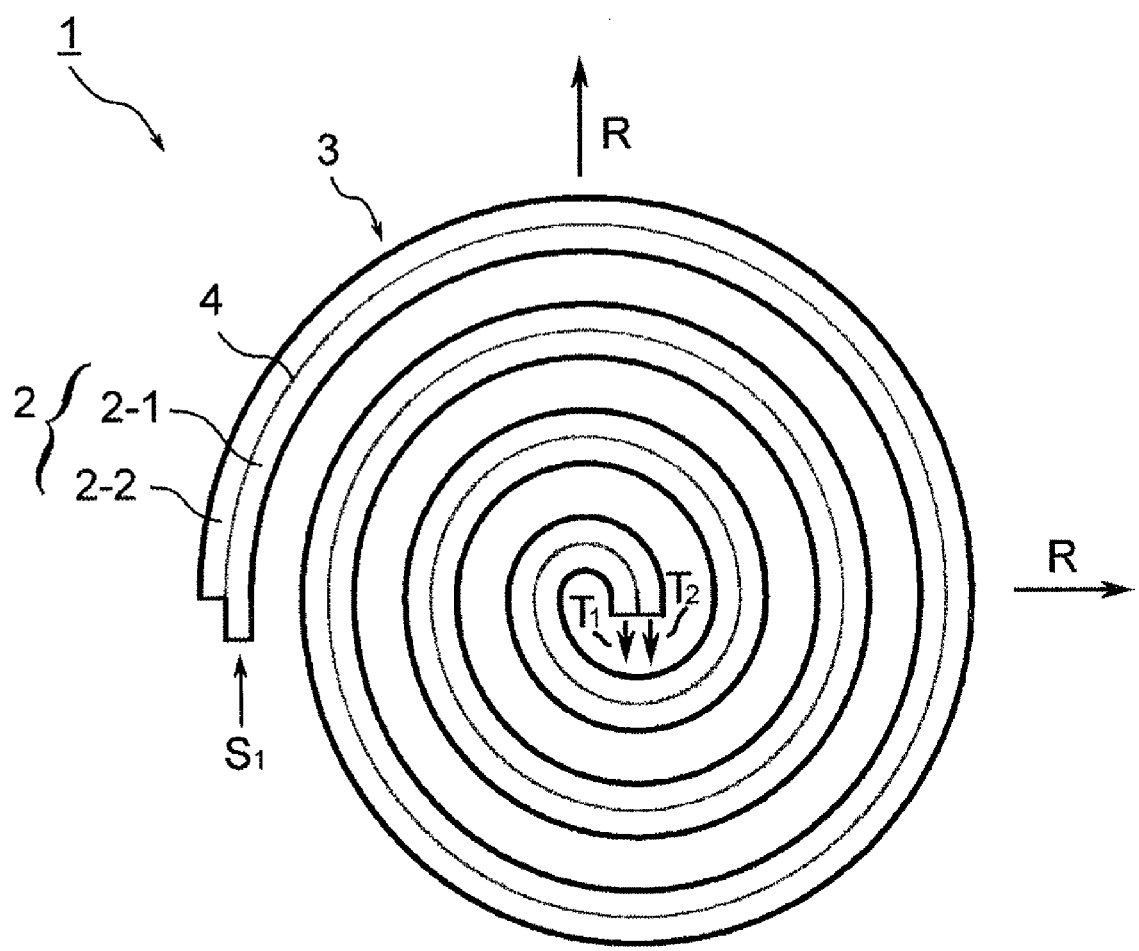
FIG. 3 is a top view of still another example of the classifying device as an exemplary embodiment of the invention.

FIGS. 1, 2 and 3 are top views of examples of the classifying device as an exemplary embodiment of the invention.

In FIG. 1, the classifying device 1 has a microchannel 2 equipped with a semicircularly curved portion 3. The microchannel 2 in FIG. 2 has the shape of concatenated semicircles. And the microchannel 2 in FIG. 3 has the shape of an Archimedean spiral. Additionally, each of the microchannels in FIGS. 1 to 3 is a microchannel having the shape of a plane curve, and the direction of its channel depth is toward the back of paper. In other words, the direction of gravity (a vertical and downward direction) is toward the back of paper.

Each microchannel is preferably shaped so that one of channels formed by partitioning the microchannel with a diaphragm is situated on the outer side relative to the direction of centrifugal force throughout its length, from the upstream to the downstream of the channel, and the other is situated on the inner side relative to the direction of centrifugal force throughout its length, from the upstream to the downstream of the channel. Suitable examples of a channel shape allowing one of channels formed by partitioning the microchannel with a diaphragm to be situated on the outer side relative to the direction of centrifugal force throughout its length include a semicircular shape, an elliptical shape and a turbinated shape (a spiral shape) Of these shapes, a turbinated shape (a spiral shape) is preferred over the others. In FIGS. 1 to 3, the direction of centrifugal force is indicated by an arrow R.

Making reference to FIGS. 1 to 3, the microchannel 2 is partitioned with a diaphragm 4 in the curved portion, and formed of a microchannel 2-1 situated on the inner side relative to the direction of centrifugal force and a microchannel 2-2 situated on the outer side relative the direction of centrifugal force.

Additionally, the shape of a microchannel in each exemplary embodiment of the invention may be either a plane curve or a space curve. Examples of a planar spiral shape include the shape of concatenated semicircles, the shape of an Archimedean spiral and the shape of a parabolic spiral, while an example of a space curve is a helical shape (a coiled spring shape).

In FIG. 2 and FIG. 3 each, a dispersion liquid of fine particles may be fed into the microchannel from one microchannel end in the center of paper, wherein the curved portion of the microchannel may be shaped to have a gradually increasing curvature radius. Contrary to this case, a dispersion liquid of fine particles may also be fed into the microchannel from one outermost end of the microchannel.

(Diaphragm)

In the classifying device as an exemplary embodiment of the invention, the curved portion of its microchannel incorporates a diaphragm provided with at least two kinds of apertured groups having different meshes and facing toward centrifugal force. The diaphragm is placed in parallel to the flow direction in the channel. When a dispersion liquid of fine particles is fed into one of the channels, the diaphragm intersects with flows of fine particles in the direction of centrifugal force or in the reverse direction by Dean vortices.

Additionally, though it is required that the diaphragm be provided in at least part of the curved portion, it is preferred from the standpoint of feeding a particles-dispersed liquid into one of the channels that the diaphragm be provided throughout the length of the microchannel.

Figure 4:
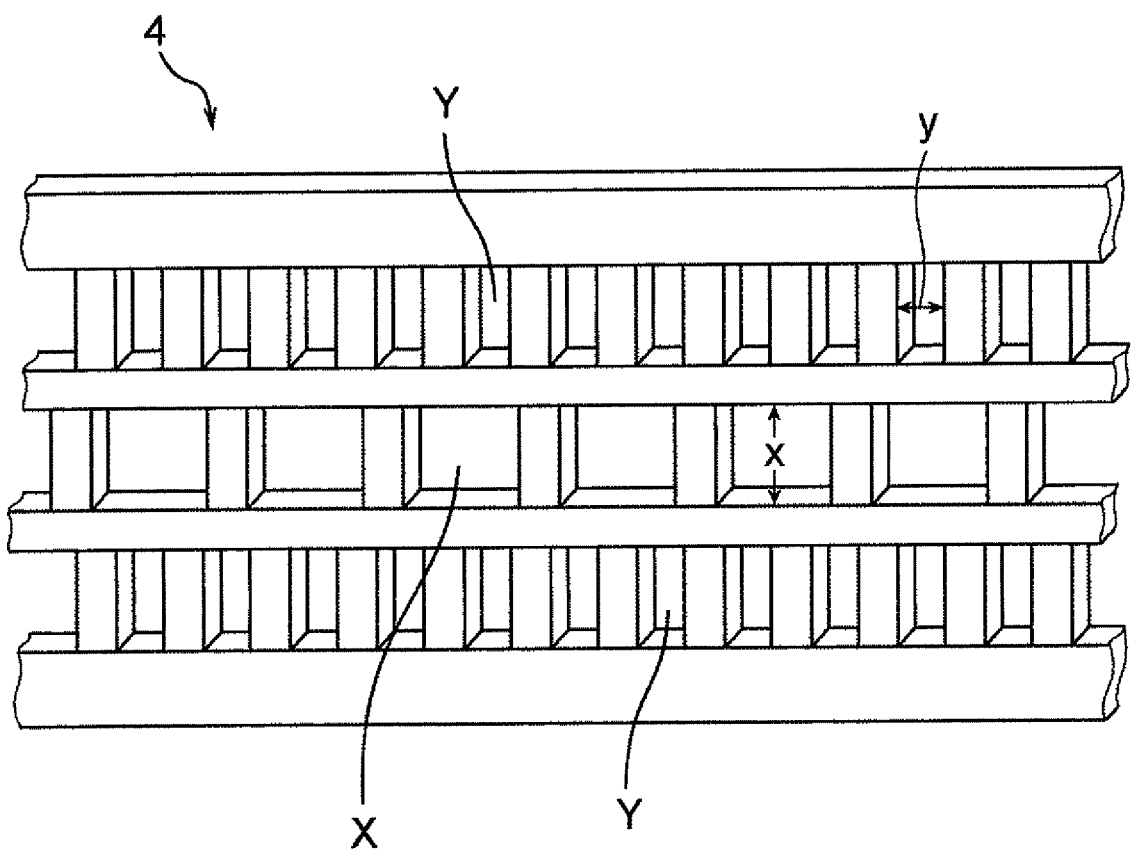
FIG. 4 is a perspective view of a diaphragm 4 under observation from the direction of an arrow A in FIG. 1.

FIG. 4 is an oblique perspective view of the diaphragm 4 observed from the direction of an arrow A in FIG. 1. Incidentally, though the diaphragm 4 has a curved shape because it is provided in the curved portion, it can be depicted as being linear in microscopic scale.

In FIG. 4, the diaphragm 4 is provided with apertured group X large in mesh and apertured group Y small in mesh. The term "mesh" as used herein refers to the maximum diameter of particles capable of passing through apertured group. In FIG. 4, the mesh of the apertured group X is represented by x, and the mesh of the apertured group Y is represented by y.

The mesh of apertured group the diaphragm has in a central region in the vertical direction differs in size from the mesh of apertured group the diaphragm has in regions located near the channel's bottom face and top face. As shown in FIG. 4, the apertured group X large in mesh are formed in the diaphragm's central region in the vertical direction, and the apertured group Y small in mesh are formed in the diaphragm in regions located near the channel's bottom face 42 and top face 41.

Incidentally, though the mesh x of apertured group X made in the diaphragm's central region in the vertical direction is large in FIG. 4 and the mesh y of apertured group Y made in the diaphragm in regions located near the channels bottom face and top face is small in FIG. 4 (x>y), exemplary embodiments of the invention should not be construed as being limited to this relation, but it is also possible as mentioned below that the mesh of apertured group in the diaphragm's central region in the vertical direction is rendered small and the mesh of apertured group located near the channel's bottom face and top face is rendered large.

Herein, the apertured group in the diaphragms central region in the vertical direction have no particular restrictions so long as apertured group with a different mesh are provided on the upper and lower sides of the apertured group in the central region, but it is preferable that the apertured group in the central region includes aperturas formed in the center in the vertical direction (the center of height) or the neighborhood thereof. In addition, it is preferable that the apertured group in the central region is provided at a location the same distance from the channel's top face and the bottom face.

On the other hand, the apertured groups located near the channel's bottom face and top face have no particular restrictions so long as they are formed at locations nearer the bottom face and the top face than the apertured group in the central region in the vertical direction, but it is preferable that the mesh of the apertured group in the vicinity of the top face is approximately equal to the mesh of the apertured group in the vicinity of the bottom face, and besides, it is preferable that the distance between the apertured group in the vicinity of the top face and the top face is equal to the distance between the apertured group in the vicinity of the bottom face and the bottom face.

Although the diaphragm shown in FIG. 4 has two kinds of apertured groups differing in mesh, diaphragms usable in exemplary embodiments of the invention have no particular restrictions so long as they each have at least two kinds of apertured groups. So, a diaphragm designed to have three kinds of apertured groups may also be employed. In point of easiness with which a diaphragm and a classifying device are made, it is advantageous to employ a diaphragm having two kinds of apertured groups.

A method of classifying particles by feeding a particles-dispersed liquid into one of the channels as shown in FIG. 1 is described below.

The microchannel 2 in its entirety is filled in advance with a dispersion medium used in a particles-dispersed liquid, and the particles-dispersed liquid is fed into one of the channels into which the microchannel 2 is partitioned with a diaphragm 4. In FIG. 1, the particles-dispersed liquid $S_1$ is fed into the microchannel 2-1 on the inner side relative to the direction of centrifugal force. The method of classifying particles by feeding a particles-dispersed liquid into a microchannel with a curved portion and causing movement of the particles to the outer side of the channel relative to the direction of centrifugal force with the aid of the centrifugal force has hitherto been known. However, as described in Ookawara et al., *Chemical Engineering Journal*, 101 (2004), pp. 171-178, a phenomena is observed in which secondary flows referred to as Dean vortices occur in a curved portion and the particles once moved to the outer side of the channel by the centrifugal force return to the inner side of the channel by the secondary flows (Dean vortices).

Figure 5:
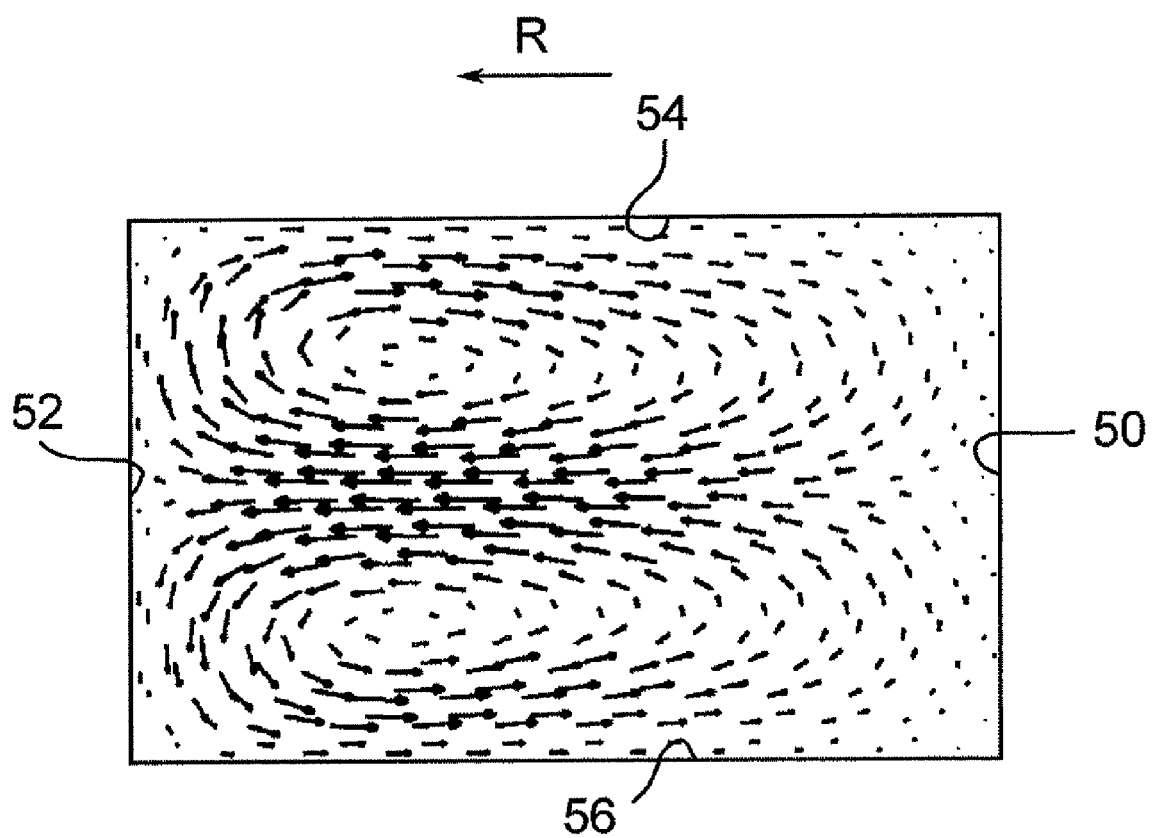
FIG. 5 is an illustration of velocity vectors of secondary flows occurring in a channel's vertical section of the curved portion of a microchannel.

FIG. 5 shows an example of velocity vectors of secondary flows occurring in a channel's vertical section of the curved portion of a microchannel. In FIG. 5, the channel is formed of an inner wall 52 on the outer side of the channel relative to the direction of centrifugal force, an inner wall 50 on the inner side of the channel relative to the direction of centrifugal force, a channel's top face 54 and a channel's bottom face 56. Incidentally, FIG. 5 is a schematic diagram of the case where fluid is fed into a microchannel having no diaphragm, and a pair of Dean vortices are formed on upper and lower sides as shown in FIG. 5. The region greatest in velocities of secondary flows is present in between the upper Dean vortex and the lower Dean vortex (the channel's central region in the vertical direction). By the velocity distribution of secondary flows occurring in the curved portion of a microchannel, there occurs a phenomenon in which, when a dispersion liquid of fine particles is fed into the microchannel, particles moved in the direction of centrifugal force by centrifugal force move again to the inner side relative to the direction of centrifugal force by undergoing the force to move them in the direction opposite to the direction of centrifugal force.

According to exemplary embodiments of the invention, when a microchannel having the diaphragm as shown in FIG. 4 is used and a dispersion liquid of fine particles is fed into a channel 2-1 on the inner side relative to the direction of centrifugal force, the fine particles undergo greatest force in the direction of centrifugal force in the channel's central region in the vertical direction by influences of centrifugal force and Dean vortices. The apertured group X large in mesh is provided in the central region in the vertical direction, and particles having sizes smaller than the mesh in the central region move in the direction of centrifugal force. Incidentally, the particles having the same size as the mesh cannot pass through the apertured group.

The particles moved into a channel 2-2 on the outer side relative to the direction of centrifugal force move again into a channel 2-1 on the inner side relative to the direction of centrifugal force while moving toward the channel's top face or bottom face. Herein, among the particles moved into the channel 2-2 on the outer side relative to the direction of centrifugal force, particles incapable of passing through the apertured group Y (particles having sizes equal to or larger than the mesh y) remain in the channel 2-2 on the outer side relative to the direction of centrifugal force, because the apertured group Y small in mesh are provided in the diaphragm regions located near the channel's bottom and top faces.

In the lower reaches of the curved portion, discharged liquids ($T_1$, $T_2$) from the channel 2-1 on the inner side relative to the direction of centrifugal force and the channel 2-2 on the outer side relative to the direction of centrifugal force are collected independently. Thus, the discharged liquid $T_1$ from the channel 2-1 on the inner side relative to the direction of centrifugal force contains coarse particles and fine particles, while the discharged liquid $T_2$ from the channel 2-2 on the outer side relative to the direction of centrifugal force contains particles having sizes between the mesh of the apertured group X in the diaphragm's central region in the vertical direction and the mesh of the apertured group Y in the diaphragm regions located near the channel's bottom and top faces.

In other words, the apertured group in the central region in the vertical direction defines the upper size limit of particles to be classified, while the apertured group in proximity to bottom and top faces defines the lower size limit of particles to be classified.

Figure 6A:
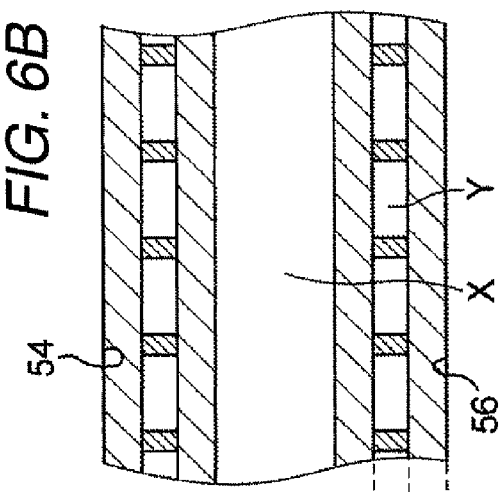
FIGS. 6A to 6C are vertical cross-sectional views of a channel and a plan view of a diaphragm for illustrating another aspect of the diaphragm suitably used in an exemplary embodiment of the invention.
Figure 6B:
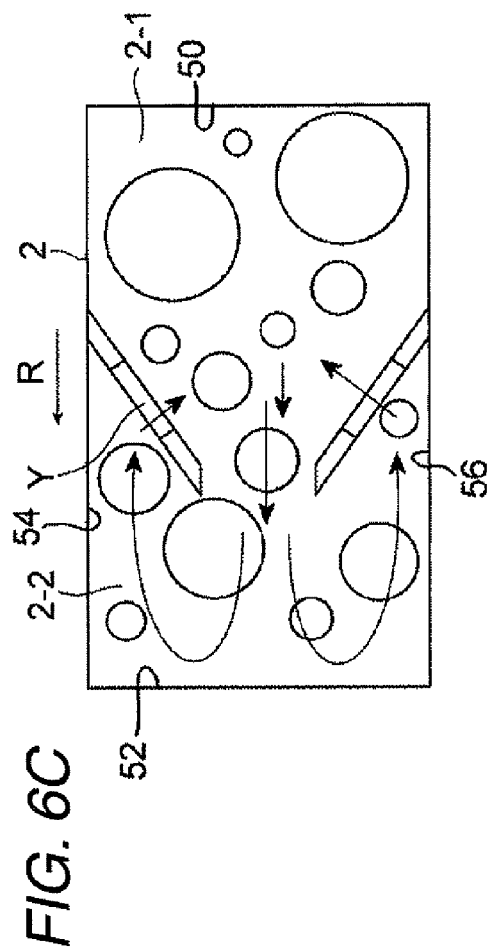
Figure 6C:
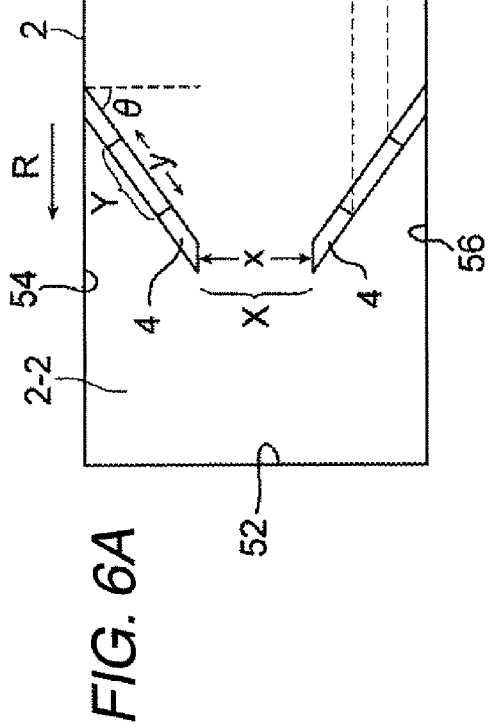

In FIGS. 6A to 6C, another aspect of the diaphragm used suitably in an exemplary embodiment of the invention is illustrated with a vertical cross-sectional view of the channel and a plan view of the diaphragm.

FIG. 6A is the vertical cross-sectional view of the channel, and FIG. 6B is the plan view of the diaphragm.

On viewing FIG. 6A, the diaphragm sloping away from the top face 54 and bottom face 56 of the channel, respectively, in the direction of centrifugal force (indicated by an arrow R) and forming an angle of θ with the vertical to the channel's top and bottom faces is installed in the microchannel. The slope angle θ of the diaphragm is preferably from 0° or about 0° to 60° or about 60°, far preferably from 25° to 45°, further preferably from 25° to 35°.

On viewing FIG. 6C, particles can move along a diaphragm 4 when the diaphragm slopes in the direction of centrifugal force; as a result, the diaphragm's apertures situated at the center in the vertical direction are prevented from becoming clogged with particles.

The diaphragm's central region in the vertical direction has apertured group X large in mesh, while the diaphragm's regions located near channel's bottom and top faces have apertured group Y small in mesh. In the FIG. 6A, these meshes are indicated by x and y, respectively.

FIG. 6C is a conceptual illustration of a case where a particles-dispersed liquid is fed into one of the microchannels of the classifying device shown in FIG. 6A. When a particles-dispersed liquid is fed into the microchannel 2-1 on the inner side relative to the direction of centrifugal force, particles are moved to the microchannel on the outer side relative to the direction of centrifugal force by the centrifugal force. At this time, particles larger in size than the mesh x cannot pass through the apertured group X and remain in the microchannel 2-1. On the other hand, particles smaller in size than the mesh x pass through the apertured group X and move to the microchannel 2-2 on the outer side relative to the direction of centrifugal force. On the particles having squeezed through the apertured group X, Dean vortices exert force to move them upward or downward and further in the direction opposite to the direction of centrifugal force. Particles smaller in size than the mesh y can pass through the apertured group Y, and move to the microchannel 2-1, while particles larger in size than the mesh y cannot pass through the apertured group Y, and remain in the microchannel 2-2.

Therefore, of the two kinds of apertured groups (apertured group X and apertured group Y) the diaphragm has, the apertured group X define the upper size limit of particles to be classified and the apertured group Y define the lower size limit of particles to be classified.

Figure 7:
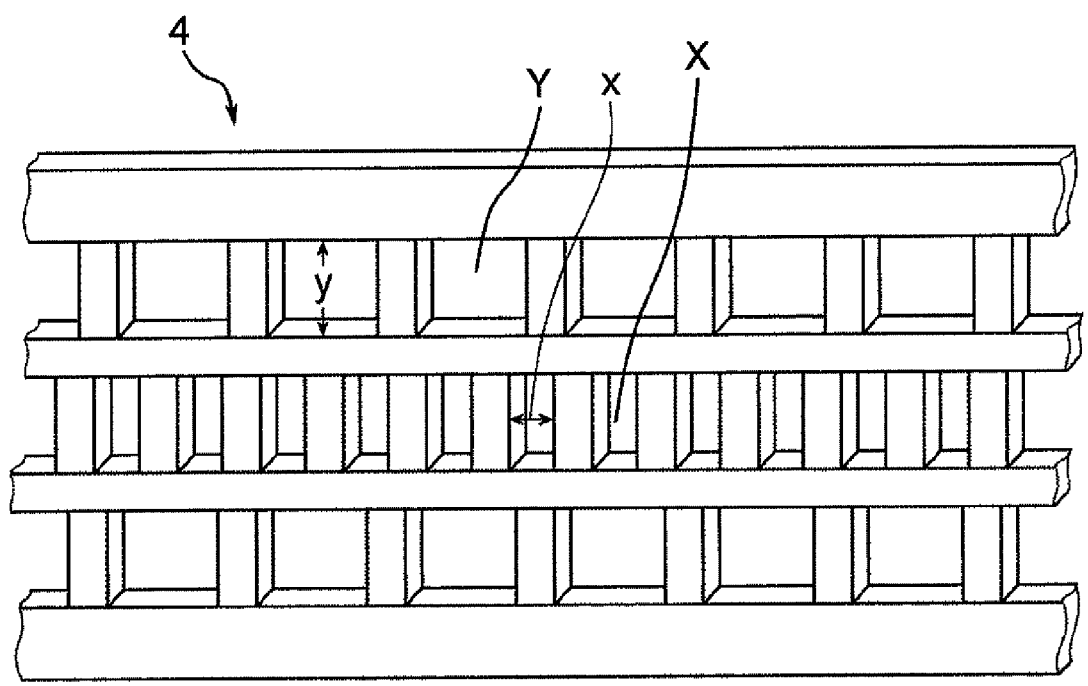
FIG. 7 is a perspective view showing another aspect of the diaphragm used in the classifying device as an exemplary embodiment of the invention.
Figure 8A:
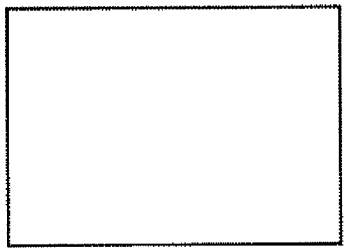
FIGS. 8A to 8L are conceptual illustrations of thin-layer patterns for forming the classifying device shown in FIG. 1.
Figure 8G:
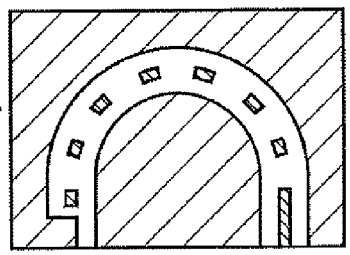
Figure 8B:
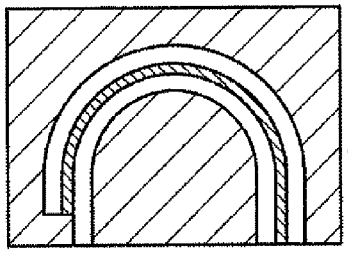
Figure 8H:
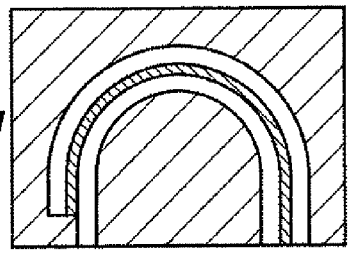
Figure 8C:
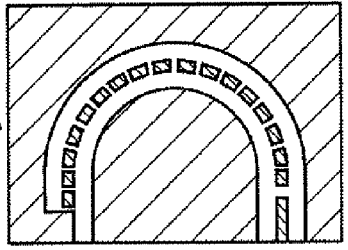
Figure 8I:
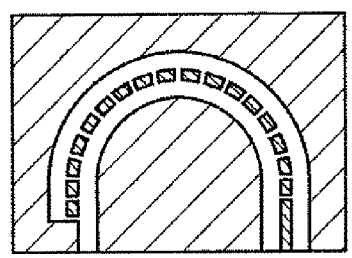
Figure 8D:
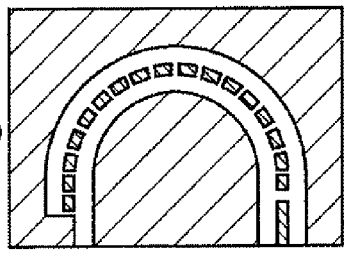
Figure 8J:
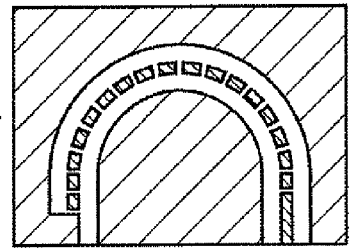
Figure 8E:
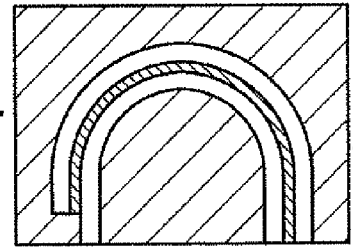
Figure 8K:
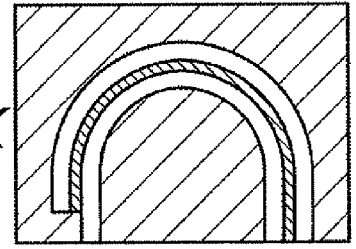
Figure 8F:
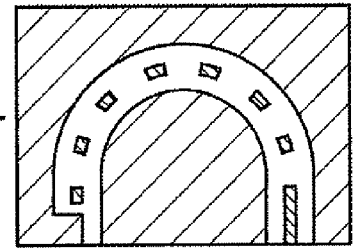
Figure 8L:
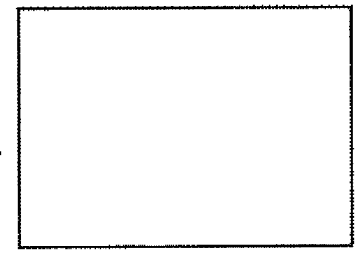

FIG. 7 is an oblique perspective view showing another aspect of a diaphragm usable in the classifying device as an exemplary embodiment of the invention. The diaphragm in FIG. 7 is illustrated by observation from the direction of the arrow A in FIG. 1.

In FIG. 7, the apertured group X small in mesh is provided in the diaphragm's central region in the vertical direction, and the apertured group Y large in mesh is provided in the diaphragm in regions located near the channel's bottom and top faces.

A classification method using a classifying device as shown in FIG. 7 is described below.

In the classifying device as shown in FIG. 7, a particles-dispersed liquid is fed into a channel on the outer side relative to the direction of centrifugal force. By the influences of Dean vortices as the secondary flows, particles smaller in size than the mesh of the apertured group provided in the diaphragms regions near the channel's top and bottom faces are moved into the microchannel on the inner side relative to the direction of centrifugal force. Of the particles moved into the microchannel on the inner side relative to the direction of centrifugal force, particles smaller in size than the mesh of the apertured group provided in the diaphragm's central region in the vertical direction of the channel are moved again into the microchannel on the outer side relative to the direction of centrifugal force by the centrifugal force.

Therefore, the upper size limit of particles to be classified by the channel on the inner side relative to the direction of centrifugal force is defined by the apertured group provided in diaphragm regions near the channel's top and bottom faces, and the lower size limit of particles to be classified is defined by the apertured group in the diaphragm's central region in the vertical direction.

In the classification method as an exemplary embodiment of the invention, it is preferable that fluid is fed so as to have a Dean number of 8 or higher in the curved portion of a microchannel. Herein, the term "Dean number (De)" is a dimensionless number which becomes important in taking centrifugal force into account as is the case in a curved-tube flow, and given by the following equation.

$$De = \left(\frac{\rho DV}{\mu}\right)\sqrt{\frac{L}{2R}}$$

D(m): typical length
V(m/sec): flow velocity
$\rho$(kg/m$^3$): particle density
$\mu$(Pa·s): viscosity coefficient
L(m): channel length
R(m): radius of curvature The Dean number is preferably 8 or about 8 or higher, far preferably from 10 to 300, further preferably from 10 to 50.

The Dean numbers in the range specified above are preferred because they contribute to enhancement of classification efficiency.

It is advantageous to achieve a Dean number in the foregoing range by choosing a channel diameter, a flow velocity, a particle density, a channel length, a radius of curvature and so on as appropriate.

And it is preferable that a particles-dispersed liquid is infused into a microchannel under pressure by using a microsyringe, a rotary pump, a screw pump, a centrifugal pump, a piezo pump or the like.

The rate at which a particles-dispersed liquid is fed into a microchannel is preferably from 0.01 to 1,000 ml/hr, far preferably from 10 to 300 ml/hr.

Next, the particles-dispersed liquid is described below.

The particles-dispersed liquid is preferably in a state that particles having their volume-average diameter in a range of 0.1 μm to 1,000 μm are dispersed in a medium liquid.

It is essential for the particles only that the volume-average diameter be in the range of 0.01 μm to 1,000 μm, and particles of any kind, e.g., resin particles, inorganic particles, metal particles, ceramic particles or so on, may be adequately used.

The volume-average diameter of particles is preferably from 0.1 μm to 1,000 μm as mentioned above, far preferably from 0.1 μm to 500 μm, further preferably from 0.1 μm to 200 μm, particularly preferably from 1.0 μm to 50 μm. Particles having a volume-average diameter of 1,000 μm or below are preferred because they resist clogging the channel and the apertures in the diaphragm. In addition, particles having a volume-average diameter of 1.0 μm or above are preferred because they resist depositing on the inner wall of the channel.

Although the particles have no particular restriction on the shape, there are cases where the possibility of clogging becomes high when particles have an acicular shape and their long axes are larger than a quarter of a channel width. From this viewpoint, the ratio between the long axis length and the short axis length of fine particles each (long axis length/short axis length) is preferably from 1 to 50, far preferably from 1 to 20. Additionally, it is preferred that the channel width, the channel diameter or the like be chosen appropriately to suit the particle size and shape.

The kinds of particles to be classified may include those recited below, but are not limited to them. Examples of particles include fine particles of a polymer, crystals or aggregates of an organic substance like pigment, crystals or aggregates of an inorganic substance, fine particles of a metal, and fine particles of a metal compound such as a metal oxide, a metal sulfide, a metal nitride or the like. In addition, particles of rubber, particles of wax (fine-particle wax), hollow particles and the like, regardless of whether inside pores are present or not, may be given as other examples.

Examples of a polymer formed into fine particles include polyvinyl butyral resin, polyvinyl acetal resin, polyarylate resin, polycarbonate resin, polyester resin, phenoxy resin, polyvinyl chloride resin, polyvinylidene chloride resin, polyvinyl acetate resin, polystyrene resin, acrylic resin, methacrylic resin, styrene-acrylic resin, styrene-methacrylic resin, polyacrylamide resin, polyamide resin, polyvinyl pyridine resin, cellulose resins, polyurethane resin, epoxy resin, silicone resin, polyvinyl alcohol resin, casein, vinyl chloride-vinyl acetate copolymer, modified vinyl chloride-vinyl acetate copolymer, vinyl chloride-vinyl acetate-maleic anhydride copolymer, styrene-butadiene copolymer, vinylidene chloride-acrylonitrile copolymer, styrene-alkyd resin, and phenol-formaldehyde resin.

Examples of a metal or a metal compound formed into fine particles include carbon black, metals such as zinc, aluminum, copper, iron, nickel, chromium and titanium, alloys of two or more of these metals, metal oxides such as $TiO_2$, $SnO_2$, $Sb_2O_3$, $In_2O_3$, ZnO, MgO and iron oxides, compounds of those metals, metal nitrides such as silicon nitride, and combinations of two or more of those substances.

Examples of rubber formed into fine particles include nitrile rubber, styrene rubber and isobutylene rubber. Levigation may be performed by emulsion polymerization or a mechanical operation such as freeze or cold grinding.

As the fine-particle wax, it is possible to use wax levigated by any of the heretofore known methods using the emulsifier or the dispersing machine as described in *Hanno Kogaku Kenkyu-Kai Report*-1 (chemical reaction engineering society report-1) entitled "Nyuka-Bunsan Gijutsu to Kobushi Biryushi no Biryushikei Seigyo Chapter III" (emulsification-dispersion techniques and particle size controlling of polymer microparticle chapter III), published by Kobunshi Gakkai (The Society of Polymer Science, Japan) (March, 1995). In addition, it is also possible to use fine-particle wax (release agent) prepared by a method of adding a release agent to an appropriate solvent in which the release agent is insoluble at room temperature but soluble when heated, heating the resulting admixture to make a solution, and then precipitating the release agent out of the solution as fine particles by gradually cooling the solution to room temperature (a dissolution precipitation method), or a method of making particles in a vapor phase by heating and evaporating a release agent in an inert gas like helium, then recovering the particles by depositing them on cooled film or the like, and further dispersing the particles in a solvent (a vapor deposition method).

In the foregoing preparation of fine-particle wax, finer particles may be obtained by combination with a mechanical grinding method using a medium or the like.

Examples of resin used as a raw material of the fine-particle wax include low-molecular-weight polypropylene, low-molecular-weight polyethylene, and other various kinds of wax including vegetable wax such as carnauba wax, cotton wax, haze wax or rice wax, animal wax such as beeswax or lanolin, mineral wax such as ozokerite or cercine, and petroleum wax such as paraffin, microcrystalline wax or petrolatum. In addition to such natural wax, synthetic hydrocarbon wax such as Fischer-Tropsch wax may be given as another example. Of these resins usable as raw materials of the fine-particle wax, low-molecular-weight polypropylene, low-molecular-weight polyethylene, carnauba wax and paraffin are preferred over the others.

As the hollow particles, both inorganic hollow particles and organic hollow particles may be used. As the inorganic hollow particles, hollow particles of silica type and those of silica/alumina type are preferred, while hollow particles of resin type are suitable as organic ones. In addition, the number of pores in each particle may be only one or more than one. Though hollow particles have no particular limitation of porosity, the porosity is preferably from 20% to 80%, far preferably from 30% to 70%. Examples of inorganic hollow particles include Fillite available from Japan Fillite Co., Ltd. and Cenolite available from Tomoe Engineering Co., Ltd., and examples of organic hollow particles include Expancel available from Japan Fillite Co., Ltd., ADVANCELL manufactured by SEKISUI CHEMICAL CO., LTD., SX866 (A) and SX866 (B) manufactured by JSR Corporation, and Nipol MH5055 manufactured by ZEON CORPORATION. Of these hollow particles, Expancel available from Japan Fillite Co., Ltd. are preferred over the others. In particular, thermally expansible fine particles such as Expancel DU may be used in a state of being expanded to a desired size by moderate heating.

Although these fine particles may be made by many different methods, there are many cases in which fine particles are produced in a medium liquid by synthesis, and then classified as they are. Alternatively, there may be a case where fine particles made by mechanically loosening and grinding massive particles are dispersed in a medium liquid, and then classified. In this case, loosening and grinding of massive particles are often performed in a medium liquid, so the ground particles in the medium liquid are classified as they are.

On the other hand, for classification of powder (fine particles) made by a dry method, it is required that the powder be dispersed in a medium liquid beforehand. Examples of a machine for dispersing dry powder in a medium liquid include a sand mill, a colloid mill, an attritor, a ball mill, a Dyno mill, a high-pressure homogenizer, an ultrasonic dispersing machine, a coball mill and a roll mill. Herein, it is preferred that the dispersing operation be carried out under such a condition as not to cause grinding of primary particles.

The medium liquid usable in the classification method as an exemplary embodiment of the invention has no particular restrictions, and examples thereof include water, media of water type and media of organic solvent type.

Examples of the water include ion exchange water, distilled water and electrolytic ion water. And examples of the media of organic solvent type include methanol, ethanol, n-propanol, n-butanol, benzyl alcohol, methyl cellosolve, ethyl cellosolve, acetone, methyl ethyl ketone, cyclohexanone, methyl acetate, n-butyl acetate, dioxane, tetrahydrofuran, methylene chloride, chloroform, chlorobenzene, toluene, xylene, and mixtures of two or more of the above-cited ones.

The volume-average diameter of the fine particles in exemplary embodiments of the invention, exclusive of cases where it is in the following range (1 μm or below), is a value measured with an accurate particle-size distribution measuring instrument, Coulter Multisizer 3 (made by Beckman Coulter, Inc.). Herein, the measurement is made with an aperture most suitable for the particle-diameter level of the fine particles. However, in the cases where the diameters of fine particles are 1 μm or below, the measurements are made with a laser diffraction scattering-utilized particle-size distribution measuring instrument (LS-200, made by Beckman Coulter, Inc.).

In addition, the specific gravity of the fine particles is measured with an Ultrapycnometer 1000 made by Yuasa Ionics, Inc. in accordance with a vapor-phase substitution (pycnometer method).

Further, the specific gravity of the medium liquid as recited above is measured with a specific gravity measuring kit AD-1653 made by A&D Company, Limited.

In the classification method as an exemplary embodiment of the invention, the content of particles in the particles-dispersed liquid is preferably from 0.1 to 40%, by volume, far preferably from 0.5 to 25% by volume. When the proportion of particles in the particles-dispersed liquid is 0.1% by volume or higher, the particles are recovered with efficiency. And when the proportion of particles in the dispersion liquid is 40% by volume or lower, clogging of the channel is hard to occur.

The material used for the classification device as an exemplary embodiment of the invention is preferably a material having high strength and an anticorrosion property and capable of increasing the flowability of a particles-dispersed liquid. Those usable as such a material are generally used materials including metals (e.g., iron, aluminum, stainless steel, titanium and other various kinds of metals), resins (e.g., fluorocarbon resin, acrylic resin and the like), ceramics (such as silicon) and glass (such as quartz), and it is advisable to choose from them a material appropriate to the medium of a dispersion liquid to be fed. In addition, it is also possible to enhance the corrosion resistance and to reduce flow resistance by forming film of $SiN_4$, $SiN_2$, $Al_2O_3$ or the like on the surface of a structural material of the classification device through surface modification treatment such as plasma CVD.

Fine processing technology is applicable in classifying-device making. Examples of fine processing technology applicable therein include LIGA technology using X-ray lithography (Roentogen-Lithographie Galvanik Abformung), high aspect-ratio photolithography using EPON SU-8 (trade name), micro electro discharge machining (µ-EDM), Deep RIE (Reactive Ion Etching)-utilized high aspect-ratio silicon processing, hot embossing, photo-sculpturing, laser-beam machining, ion-beam machining, and mechanical micro-cutting with a micro-tool made of a hard material like diamond. These technologies may be used alone or as combination of two or more thereof. Among these technologies, preferably applied fine processing technologies are LIGA technology using X-ray lithography, high aspect-ratio photo-lithography using EPON SU-8, micro electro discharge machining (µ-EDM) and mechanical micro-cutting. Although many of microchannels in microdevices (micro-channel devices) are generally formed by micro electro discharge machining of a structural member made of SUS (stainless steel), it is preferable that the microchannel formation is carried out by a machining technique appropriate to a material used.

For bonding members together, it is advisable to employ a precision bonding method that ensures dimensional accuracy without attended by fractures of channels and so on resulting from degradation and deformation of the member materials due to heating at high temperatures, and it is advantageous to choose solid-phase bonding (e.g., pressure-weld bonding, diffusion bonding) or liquid-phase bonding (e.g., welding, eutectic bonding, soft soldering, adhesive bonding). Concrete examples of such a bonding method include silicon direct bonding employed when silicon is used as member materials and the silicon members are bonded together, fused welding for bonding glass members together, anode bonding for bonding silicon and glass together, and diffusion bonding for bonding metals together. Bonding of ceramics requires bonding techniques other than the mechanical seal techniques as employed in the case of bonding metals together. In the alumina's case, for example, there is a method of printing a bonding agent referred to as glass solder in a thickness of the order of 80 µm by screen printing, and then performing heat treatment at a temperature of 440 to 500° C. without applying any pressure. In addition, as new techniques, surface activation bonding, direct bonding using hydrogen bonds and bonding using an HF (hydrogen fluoride) aqueous solution are known.

A classification device using silicon, for example, may be made as follows.

In the first place, a cleaned and surface-treated silicon wafer is used as the board material of a substrate, and groove for channels are formed in one principal plane of the wafer by dry plasma etching. Then, the resulting wafer is integrated with another silicon wafer by bonding the surface on the channel groove side of the silicon wafer and the surface of another wafer together by direct bonding. Further, the board material integrated by bonding is cut into chips, thereby preparing microchannel chips.

When the classifying device as an exemplary embodiment of the invention is made, bonding technology may be employed. General bonding techniques are classified into two broad categories, namely solid-phase bonding and liquid-phase bonding. Representatives of solid-phase bonding techniques in common use are pressure-weld bonding and diffusion bonding, and those of liquid-phase bonding techniques in common use are welding, eutectic bonding, soft soldering and adhesive bonding.

At the time of bonding, it is better to employ a high-precision bonding technique that ensures dimensional accuracy without causing fractures in microstructures such as channels by degradation and deformation of materials due to heating at high temperatures. Examples of such a technique include silicon direct bonding, anode bonding, surface activation bonding, direct bonding using hydrogen bonds, bonding using an HF (hydrogen fluoride) aqueous solution, Au—Si eutectic bonding, void-free bonding and diffusion bonding.

The classifying device as an exemplary embodiment of the invention is preferably formed by lamination of patterned members (thin-film patterned members). And the thickness of a patterned member is preferably from 5 to 50 µm, far preferably from 10 to 30 µm.

The classifying device as an exemplary embodiment of the invention is preferably a separator made by lamination of patterned members in which specified two-dimensional patterns are formed. Herein, it is far preferred that the patterned members be stacked in a state that their faces are brought into direct contact with each other and bonded together.

Making a separator by stacking two or more patterned members corresponding respectively to horizontal cross-sectional shapes of the classifying device is favorable because the making of the separator becomes simple and easy.

An example of a preferred method for making a separator according to an exemplary embodiment of the invention is a separator making method characterized by including (i) a process of forming on a first substrate two or more patterned members corresponding to individual cross-sectional shapes of the intended separator (a donor-substrate making process), and (ii) a process of transferring the two or more patterned members on the first substrate to a second substrate by repeated cycles of bonding and estrangement between the first substrate, on which the two or more patterned members are formed, and the second substrate (a bonding process). For this method, the manufacturing method disclosed in JP-A-2006-187684 may be referred to.

The method of making the classifying device as an exemplary embodiment of the invention is described in more detail.

(Donor-Substrate Making Process)

In an exemplary embodiment of the invention, a donor substrate is preferably made by electroforming. Herein, the term "donor substrate" refers to the substrate prepared by forming on a first substrate two or more patterned members corresponding to individual cross-sectional shapes of the intended classifying device. It is appropriate that the first substrate be made from metal, ceramic or silicon, and stainless steel or like metal may be used to advantage.

To begin with, a first substrate is prepared, and then thick-film photoresist is coated on the first substrate, exposed to light via a photomask corresponding to individual cross-sectional shapes of a separator to be made, and further developed, thereby forming resist patterns which are reverse equivalents of individual cross-sectional shapes, namely positive equivalents of negatives or vice versa. Next, the substrate with these resist patterns is immersed in a plating bath, and nickel plating, for example, is made to grow on the portion of the metal substrate surface where no photoresist cover is present. The patterned members are preferably formed from gold, copper or nickel by use of electroforming.

Next, the resist patterns are removed, and thereby patterned members corresponding to individual cross-sectional shapes of the separator are formed on the first substrate.

FIGS. 8A to 8L are conceptual illustrations of thin-film patterns for forming the classifying device shown in FIG. 1. This illustration indicates that the classifying device shown in FIG. 1 is formed by stacking 12 sheets of thin-film patterns from FIG. 8A to FIG. 8L on top of each other.

Each of the combination of thin-film patterns as in 8C and 8D and that of thin-film patterns as in 8I and 8K forms small meshes, and the combination of thin-film patterns as in 8F and 8G forms large meshes.

(Bonding Process)

The bonding process is a process of transferring two or more patterned members on the donor substrate to a target substrate by repeated cycles of bonding and estrangement between the first substrate on which the two or more patterned members are formed (donor substrate) and a second substrate (target substrate). The bonding is preferably performed by ordinary-temperature bonding or surface activation bonding.

FIGS. 9A to 9F are fabrication process chart showing an example of a fabrication method for a separator which may be used suitably as an exemplary embodiment of the invention.

Figure 9D:
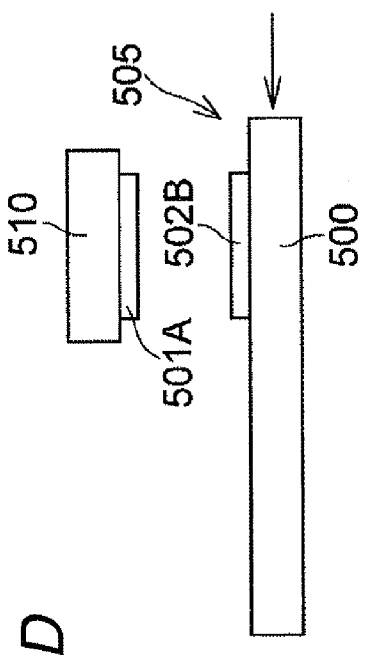
FIG. 9A to 9F are fabrication process charts showing an example of a fabrication method for a separator which can be used suitably as an exemplary embodiment of the invention.
Figure 9E:
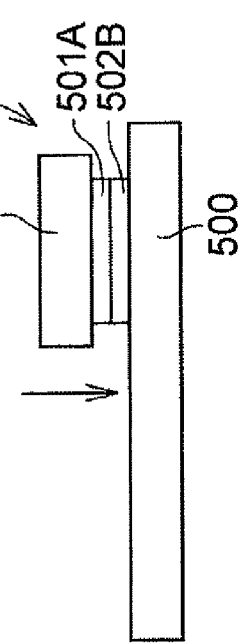
Figure 9F:
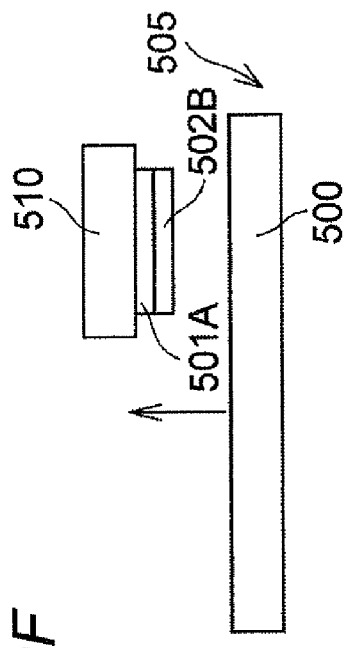
Figure 9A:
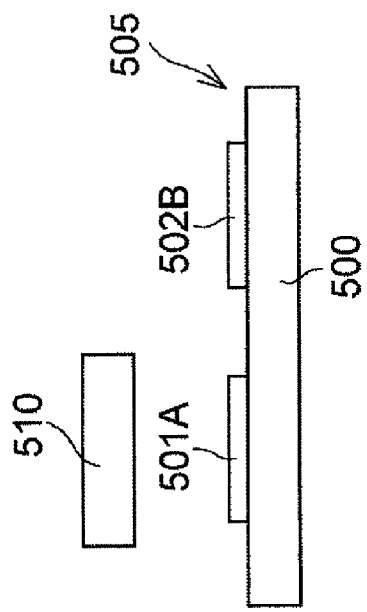

As shown in FIG. 9A, the donor substrate 505 has a metal substrate 500 as a first substrate and two or more patterned members (501) formed on the metal substrate 500, which correspond to individual cross-sectional shapes of the intended separator. Firstly, the donor substrate 505 is placed on a lower stage (not shown in the figure) in a vacuum chamber, and the target substrate 510 is placed on an upper stage (not shown in the figure) in the vacuum chamber. Successively thereto, air is exhausted from the vacuum chamber to achieve a high or ultra-high degree of vacuum. Then, the lower stage is moved relatively to the upper stage so that the patterned member 501A for the first layer, which the donor substrate 505 has, lies just under the target substrate 510. Further, the surface of the target substrate 510 and the surface of the patterned member 501A for the first layer are cleaned by irradiation with argon atomic beams.

Figure 9B:
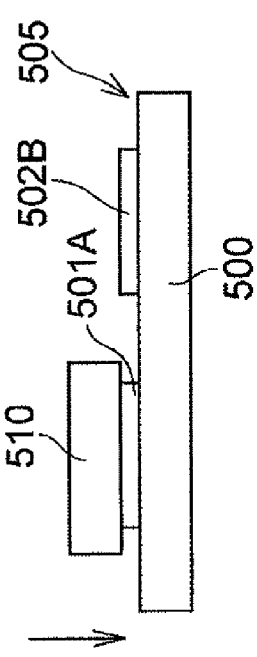

Secondly, as shown in FIG. 9B, the upper stage is moved down, and the target substrate 510 is pressed against the donor substrate 505 for a proper time (e.g., 5 minutes) under a proper load (e.g., 10 kgf/cm$^2$), thereby achieving ordinary-temperature bonding (surface activation bonding) between the target substrate 510 and the patterned member 501A for the first layer. In an exemplary embodiment of the invention, the patterned members 501A, 501B and so forth are stacked on top of each other in order of mention.

Figure 9C:
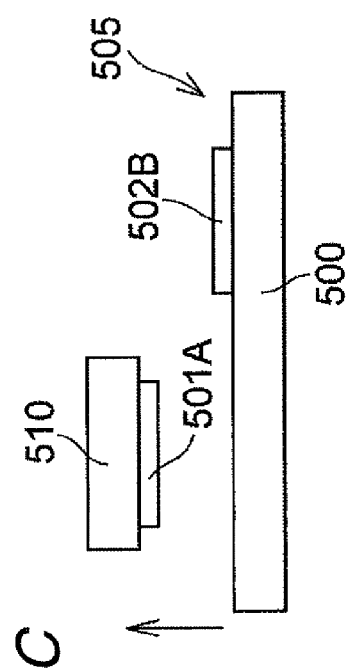

Thirdly, as shown in FIG. 9C, the upper stage is moved upward and the target substrate is estranged from the donor substrate. Thereby, the patterned member 501A for the first layer is peeled away from the metal substrate 500 (first substrate) and transferred to the side of the target substrate 510. This is because the adhesion force between the patterned member 501A for the first layer and the target substrate 510 is greater than the adhesion force between the patterned member 510A for the first layer and the metal substrate 500 (first substrate).

Fourthly, as shown in FIG. 9D, the lower stage is moved so that the patterned member 501B for the second layer, which the donor substrate 505 has, lies just under the target substrate 510, and then the surface of the patterned member 501A transferred as the first layer to the side of the target substrate 510 (the surface of the patterned member 501A on the side having been in contact with the metal substrate 500) and the surface of the patterned member 501B for the second layer are cleaned as mentioned above.

Fifthly, as shown in FIG. 9E, the upper stage is moved down, the patterned member 501A as the first layer and the patterned member 501B for the second layer are bonded together, and then, as shown in FIG. 9F, the upper stage is moved upward. Thereby, the patterned member 501B for the second layer is peeled away from the metal substrate 500 (first substrate) and transferred to the side of the target substrate 510.

In the same manner as mentioned above, other patterned members corresponding respectively to other cross-sectional shapes of the separator are also transferred to the target substrate by repeated cycle of positioning of the donor substrate 505 and the target substrate 510, bonding between these substrates and estrangement between them. The laminate transferred onto the target substrate 510 is dismounted from the upper state and the target substrate 510 is removed. Thus, the intended separator is obtained.

In the foregoing exemplary embodiment of the invention, the donor substrate is made by electroforming. Alternatively, the donor substrate may be made by using a semiconductor process. For instance, the donor substrate may also be made by preparing a substrate made of a Si wafer, providing thereon a release layer including polyimide by a spin coating method, then depositing on the release layer surface a thin film of aluminum as a constituent material of the intended separator by a sputtering method, and further subjecting the thin Al film to patterning by photolithography.

EXAMPLES

Exemplary embodiments of the invention are illustrated in more detail by reference to the following examples and comparative examples. However, the embodiments of the invention should not be construed as being limited to these examples.

Example 1

Figure 10A:
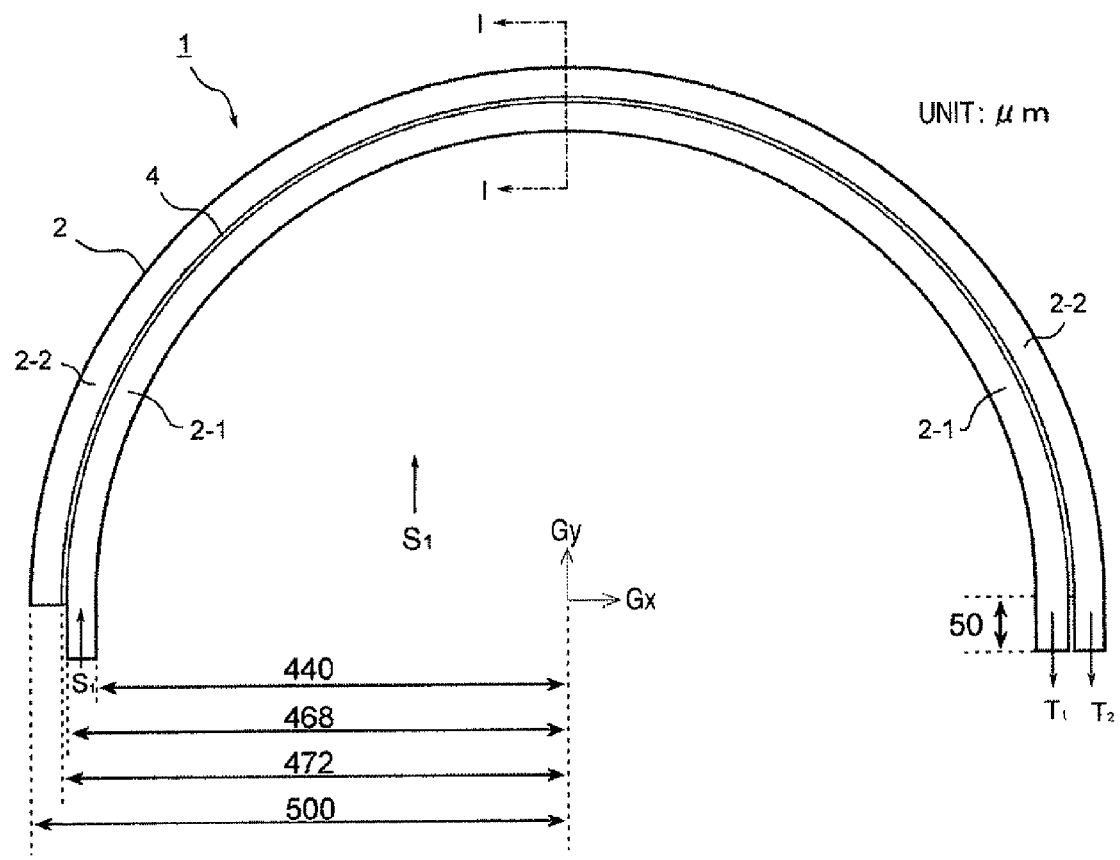
FIGS. 10A and 10B are plan views of the classifying device used in Example 1.
Figure 10B:
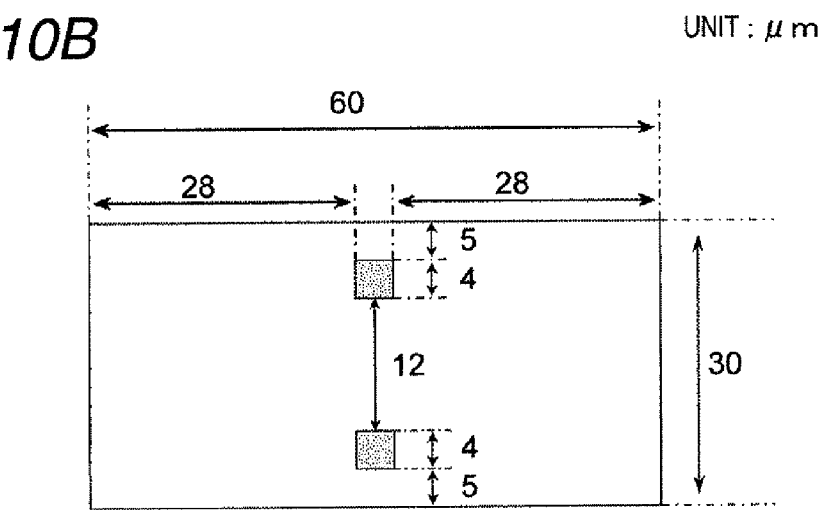

In FIGS. 10A and 10B, a plan of a classifying device used in Example 1 is shown, FIG. 10A is a top view of the classifying device 1, and FIG. 10B is a vertical cross-sectional view of the channel.

The classifying device used in Example 1 has a semicircular microchannel 2, and incorporates a diaphragm 4 into the microchannel. The diaphragm has apertured group, and the mesh of apertured group in the diaphragm's central region in the vertical direction is 12 μm, and the mesh of apertured group in the diaphragm's regions located near the channel's top and bottom faces is 5 μm.

Figure 11:
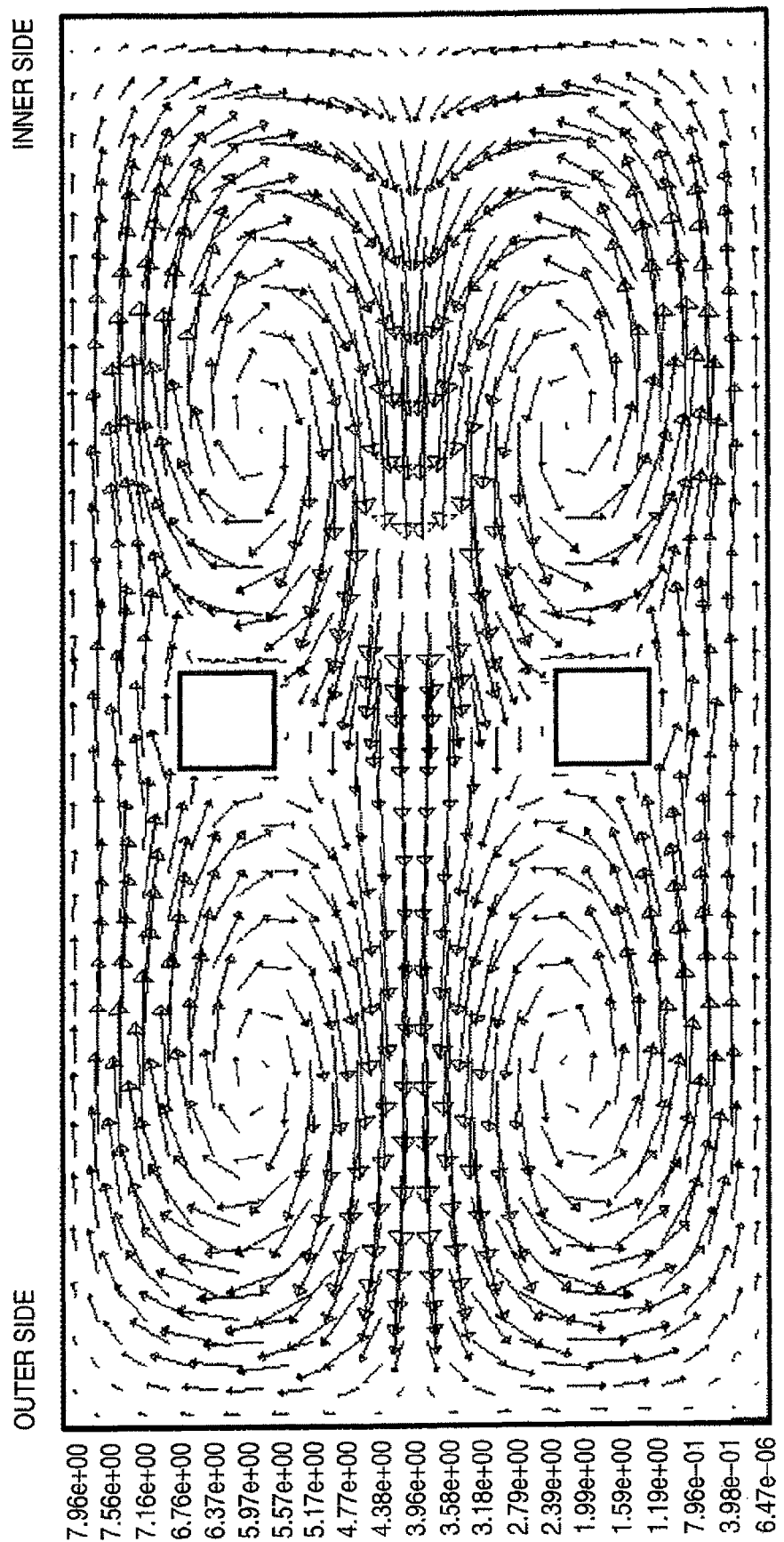
FIG. 11 is an analytic diagram of the velocity distribution in the I-I profile section of the classifying device shown in FIGS. 10A and 10B.

When the velocity distribution in the I-I profile section of the classifying device shown in FIG. 10A is analyzed, occurrence of Dean vortices is observed as shown in FIG. 11 and it is ascertained that Dean vortices occurred even when a diaphragm is provided.

Next, of the channels into which the microchannel 2 is partitioned with the diaphragm, a particles-dispersed liquid is fed into the channel 2-1 situated on the inner side of the microchannel relative to the direction of centrifugal force. Incidentally, prior to feeding the particles-dispersed liquid, the microchannel 2 is filled in advance with water as the dispersion medium of the particles-dispersed liquid. As the particles-dispersed liquid, a 3% by volume dispersion liquid of PMMA (polymethyl methacrylate, specific gravity: 1.08) is used.

Particle-size distribution in the particles-dispersed liquid ($S_1$) fed into the channel 2-1, particle-size distribution in a discharged liquid ($T_1$) from the channel 2-1 situated on the inner side relative to the direction of centrifugal forcer and particle-size distribution in a discharged liquid ($T_2$) from the channel 2-2 situated on the outer side relative to the direction of centrifugal force are determined. Results obtained are shown in FIG. 12.

Comparative Example 1

In Comparative Example 1, classification is carried out using the same device as in Example 1, except that no diaphragm is incorporated into the microchannel. In both Example 1 and Comparative Example 1, the particles-dispersed liquid is fed into the inner side of the channel relative to the direction of centrifugal force.

Figure 12:
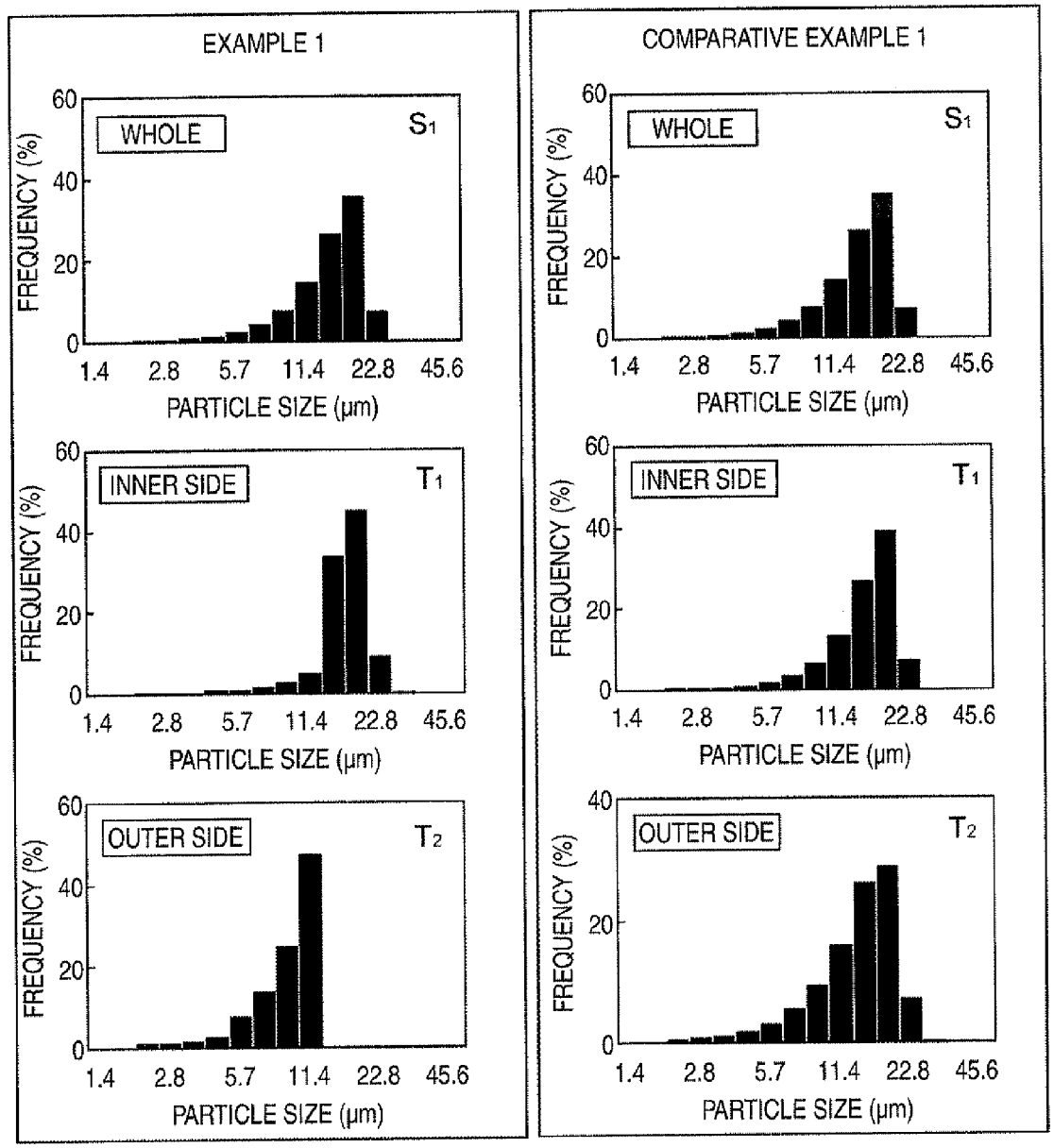
FIG. 12 is measurement results of particle-size distributions of Samples $S_1$, $T_1$ and $T_2$ in each of Example 1 and Comparative Example 1.

Results obtained are shown in FIG. 12.

Samples ($T_1$, $T_2$) obtained from the discharge ports through classification in Example 1 are compared with those through classification in Comparative Example 1, respectively. As a result of comparisons, it is found that, in the classifying device of Example 1, coarse particles having sizes greater than 12 μm are completely absent in the sample $T_2$ discharged from the channel situated on the outer side relative to the direction of centrifugal force. On the other hand, in the sample $T_1$ discharged from the channel situated on the inner side relative to the direction of centrifugal force, coarse particles greater in size than the mesh of apertured group (mesh: 12 μm) in the diaphragm's central region in the vertical direction and fine particles having passed through apertured group in the central region in the vertical direction, having been moved back by Dean vortices and having passed through apertured group in the diaphragm regions located near the channel's top and bottom faces (mesh: 5 μm) are present as a mixture.

By contrast, classification effect is hardly observed in the classifying device of Comparative Example 1 because of the influence of secondary flows by Dean vortices.

Example 2

Figure 13:
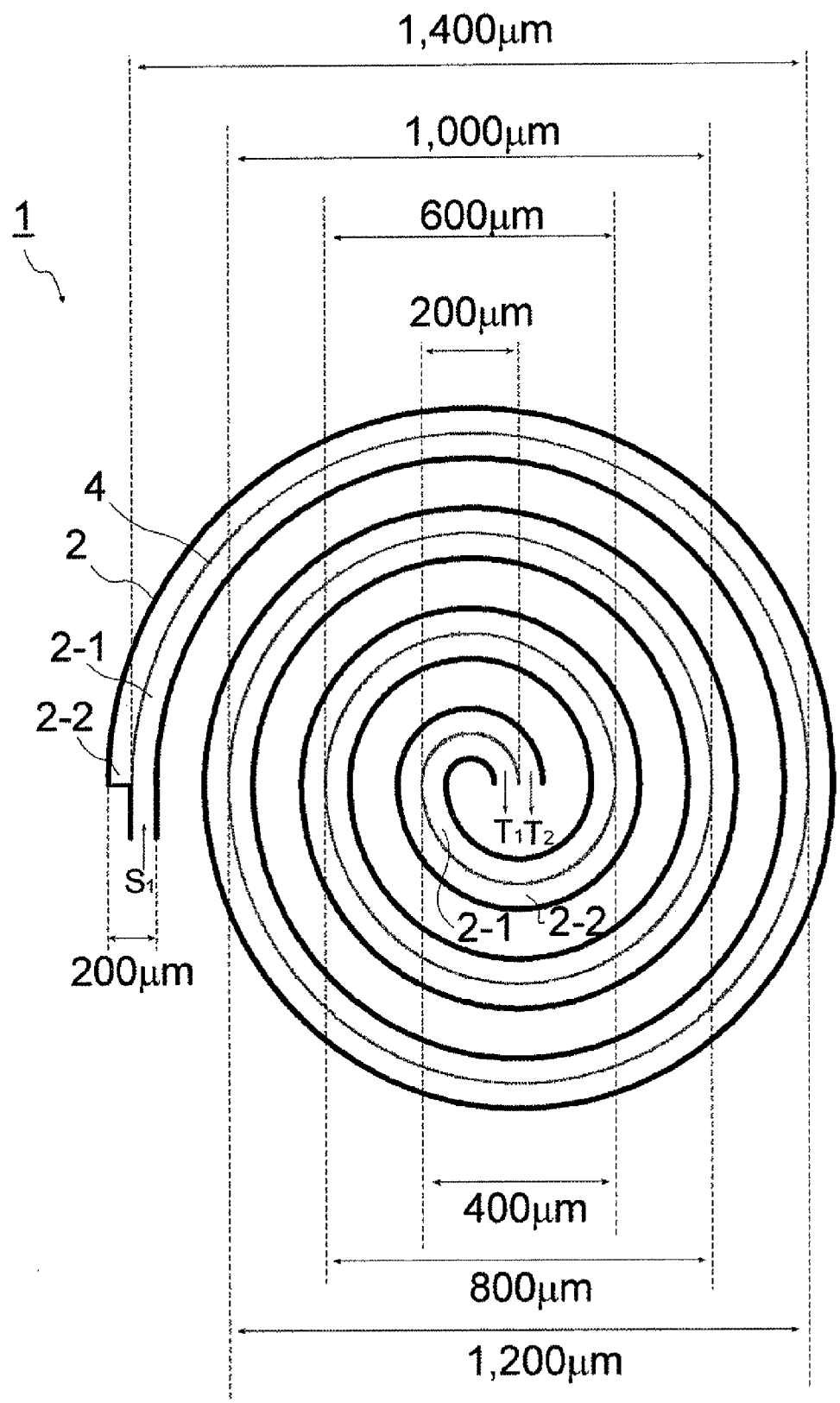
FIG. 13 is a plan view of the classifying device used in Example 2.

A plan view of the classifying device used in Example 2 is shown in FIG. 13. The microchannel of the classifying device shown in FIG. 13 has a rectangular profile section with a width of 200 μm and a height of 100 μm.

Figure 14:
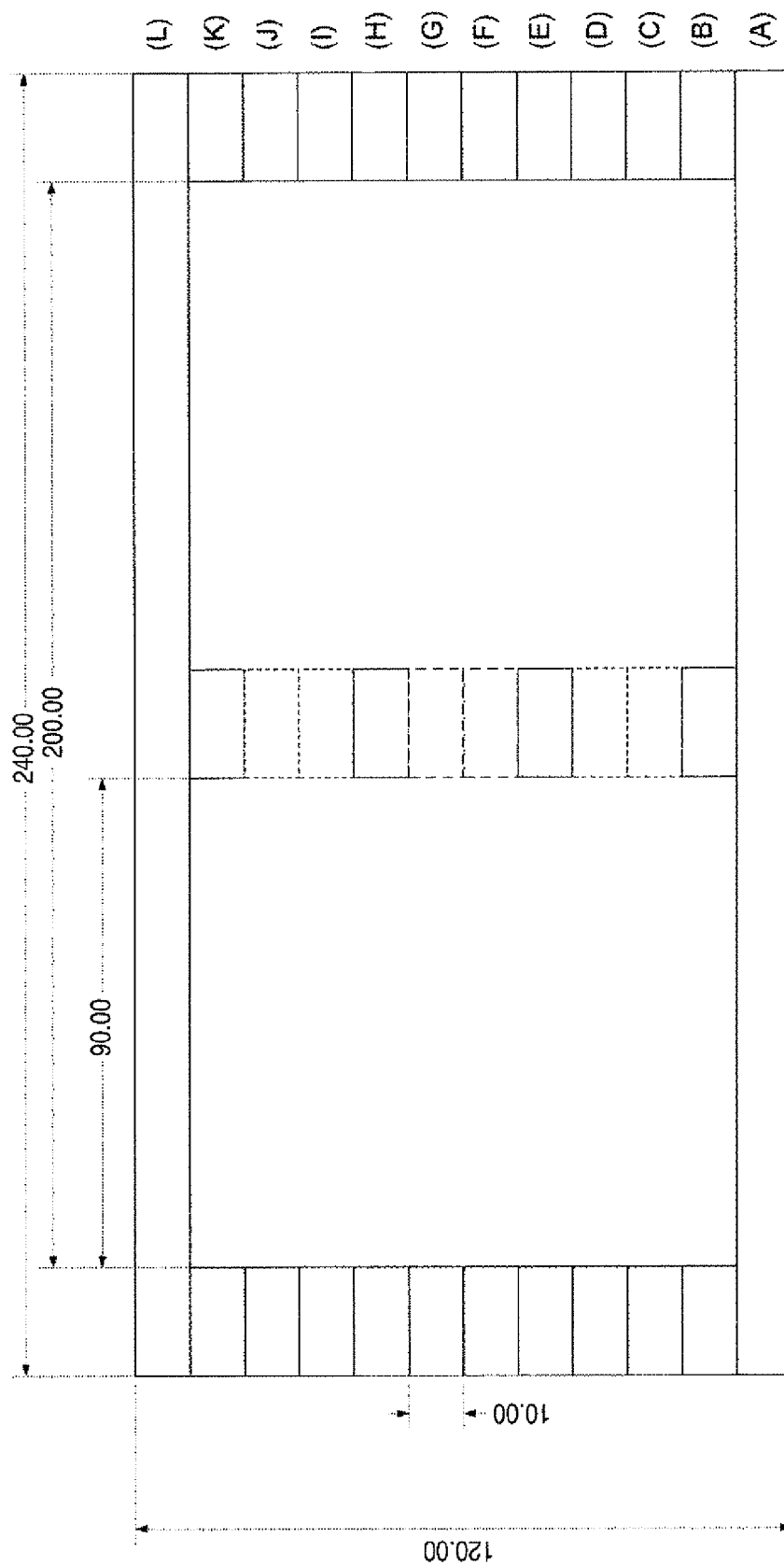
FIG. 14 is a diagram of the channel's profile section along the centrifugal force in a curved portion of the classifying device used in Example 2.

A channel's profile section along the centrifugal force in a curved portion of the classifying device used in Example 2 is shown in FIG. 14. The classifying device used in this example is fabricated by lamination of 12 patterned members.

Figure 15:
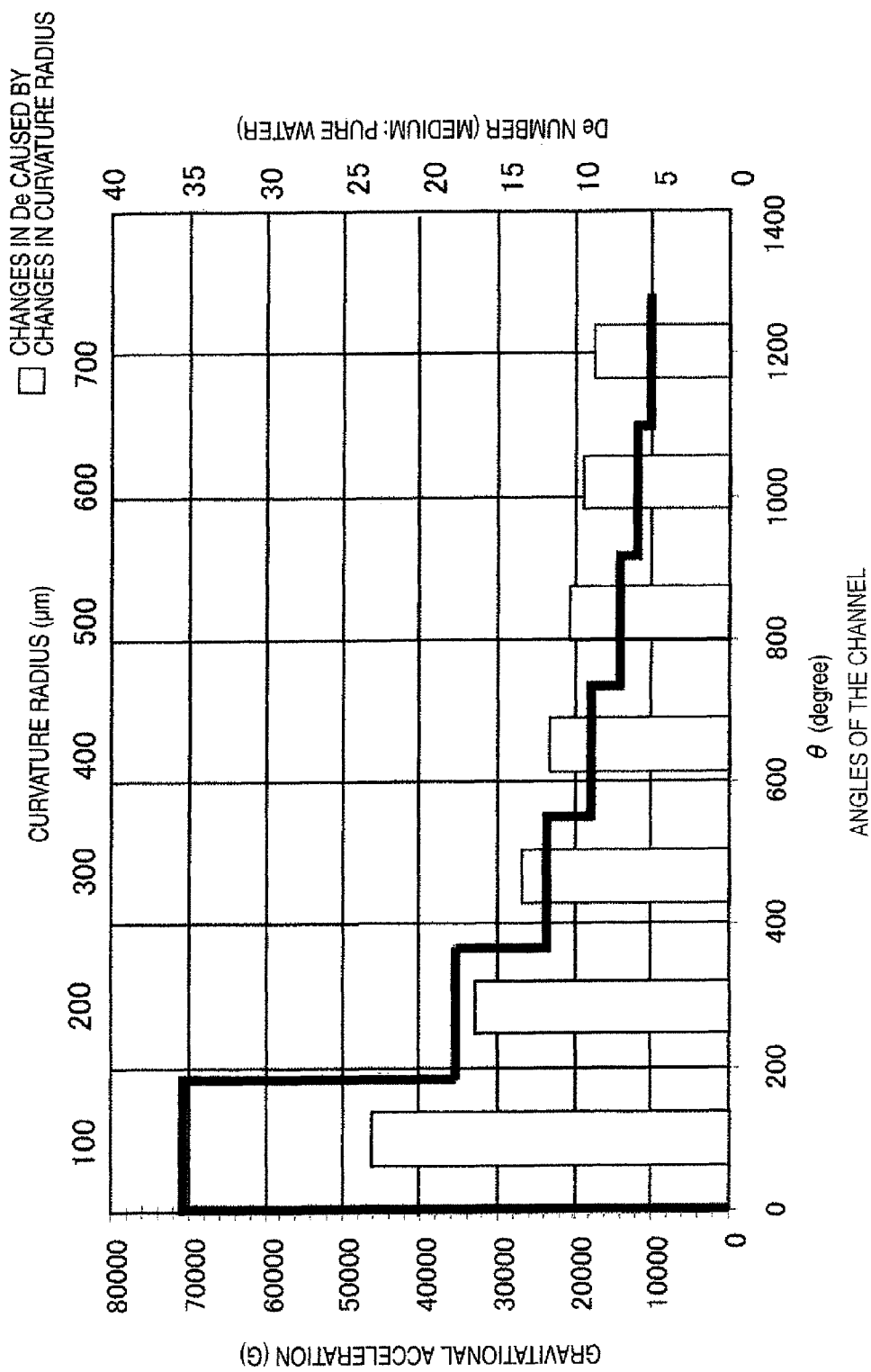
FIG. 15 is a graph showing a relation between centrifugal forces and angles of the channel in the classifying device of Example 2.

The classifying device shown in FIG. 13 assumes the shape of concatenated semicircles. Characteristic values of the classifying device are shown in Table 1. In addition, the curvature radius R (μm) and Dean number of each semicircular channel are shown in Table 2. In FIG. 15, the relation between centrifugal forces and angles of the channel in the classifying device of Example 2 is shown.

TABLE 1

| | |
|---|---|
| Rectangular channel width [μm] | 200 |
| Rectangular channel height [μm] | 100 |
| Channel area [m$^2$] | $1 \times 10^{-8}$ |
| Flow rate [ml/min] | 5 |
| Flow velocity V [m/s] | 4.17 |
| Total channel length L [mm] | 7.7 |
| Solution density ρ [kg/m$^3$] | 998 |
| Viscosity coefficient μ [Pa/s] | 0.007 |
| Equivalent hydraulic diameter (typical length) D [m] | $1.33 \times 10^{-4}$ |

TABLE 2

| Step | R [μm] | De |
|---|---|---|
| 1 | 100 | 23.31 |
| 2 | 200 | 16.48 |
| 3 | 300 | 13.46 |
| 4 | 400 | 11.65 |
| 5 | 500 | 10.42 |
| 6 | 600 | 9.52 |
| 7 | 700 | 8.81 |
| Mean value of all the steps | 400 | 11.65 |

As shown in FIG. 15, it is ascertained that variations in Dean number are almost parallel to changes in centrifugal force.

Figure 16:
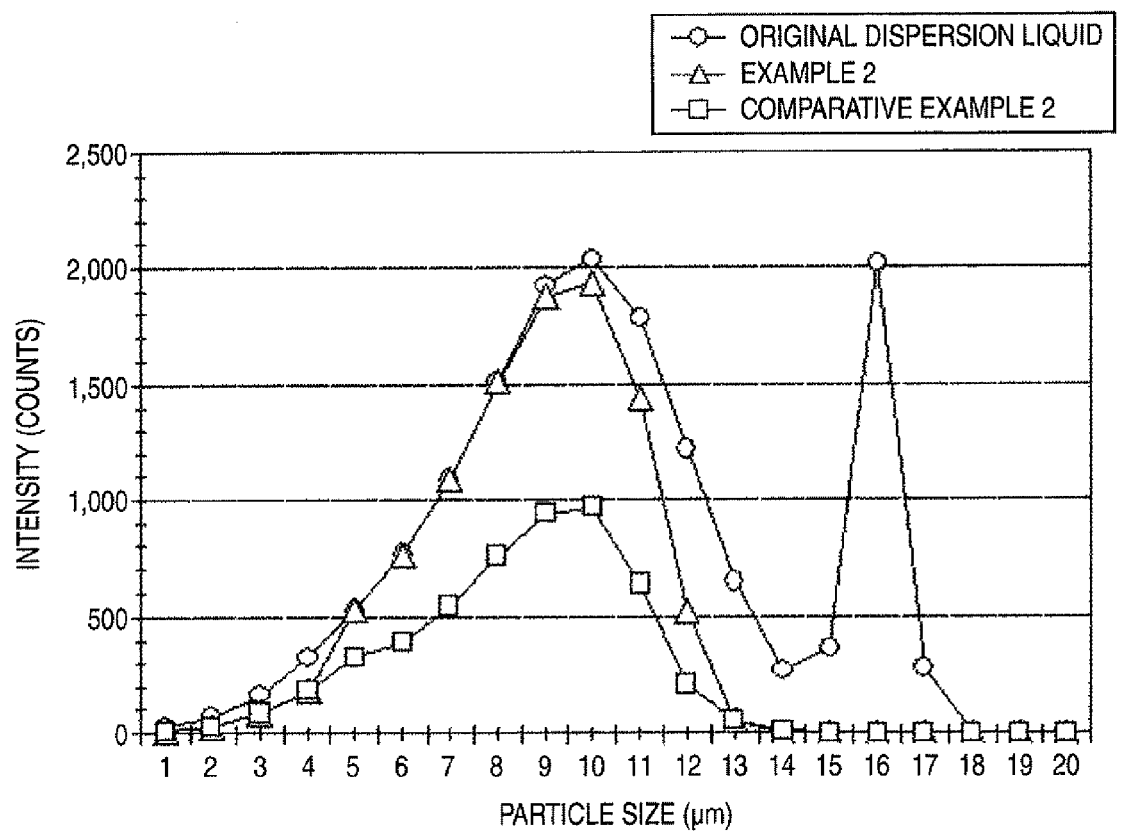
FIG. 16 shows results in Example 2.

An aqueous dispersion of toner particles having the particle-size distribution shown in FIG. 16 (original dispersion liquid, 3% by volume) is used as a sample, and fed into the inner side of the outermost channel relative to the direction of centrifugal force in the classifying device of Example 2. Incidentally, prior to the feeding of the particles-dispersed liquid, the channels are filled in advance with water as the dispersion medium.

Discharged liquid ($T_2$) from the innermost microchannel on the outer side relative to the direction of centrifugal force is collected, and size distribution of the particles contained in the discharged liquid is measured with Multisizer 3 (made by Beckman Coulter, Inc.). The measurement result obtained is shown in FIG. 16. Incidentally, the mesh of apertured group in the diaphragm's central region in the vertical direction is 12 μm, and the mesh of apertured group in the diaphragm's regions located near the channel's top and bottom faces is 5 μm. These meshes are obtained by making adjustments to pattern widths in the combination of 8C with 8D, and in combinations of 8F with 8G and 8J with 8K of FIGS. 8A to 8L, respectively (see FIG. 4 and FIGS. 8A to 8L).

In addition, the same device as in Example 2, except that no diaphragm is incorporated into the microchannel, is used in Comparative Example 2, discharged liquid ($T_2$) from the channel on the outer side relative to the direction of centrifugal force is collected, and a particle-size distribution curve of the discharged liquid is determined as in the case of Example 2.

In addition, the collection rate and the error rate in the discharge liquid $T_2$ of each of Example 2 and Comparative Example 2 are shown in FIG. 16.

Herein, the term "collection rate" is defined as the ratio between the collected particles which have their sizes in the range of 5 to 12 μm and the particles which are contained in the original dispersion liquid and have their sizes in the range of 5 to 12 μm. And the term "error rate" is defined as the proportion (% by number) of the particles whose sizes are outside the range of 5 to 12 μm in the collected particles.

As a result, it is found that the classification carried out using the classifying device of Example 2 allow achievement of a higher collection rate of particles having their sizes in the range of 5 to 12 μm and a lower error rate than the classification carried out using the device of Comparative Example 2.

Example 3

Figure 17:
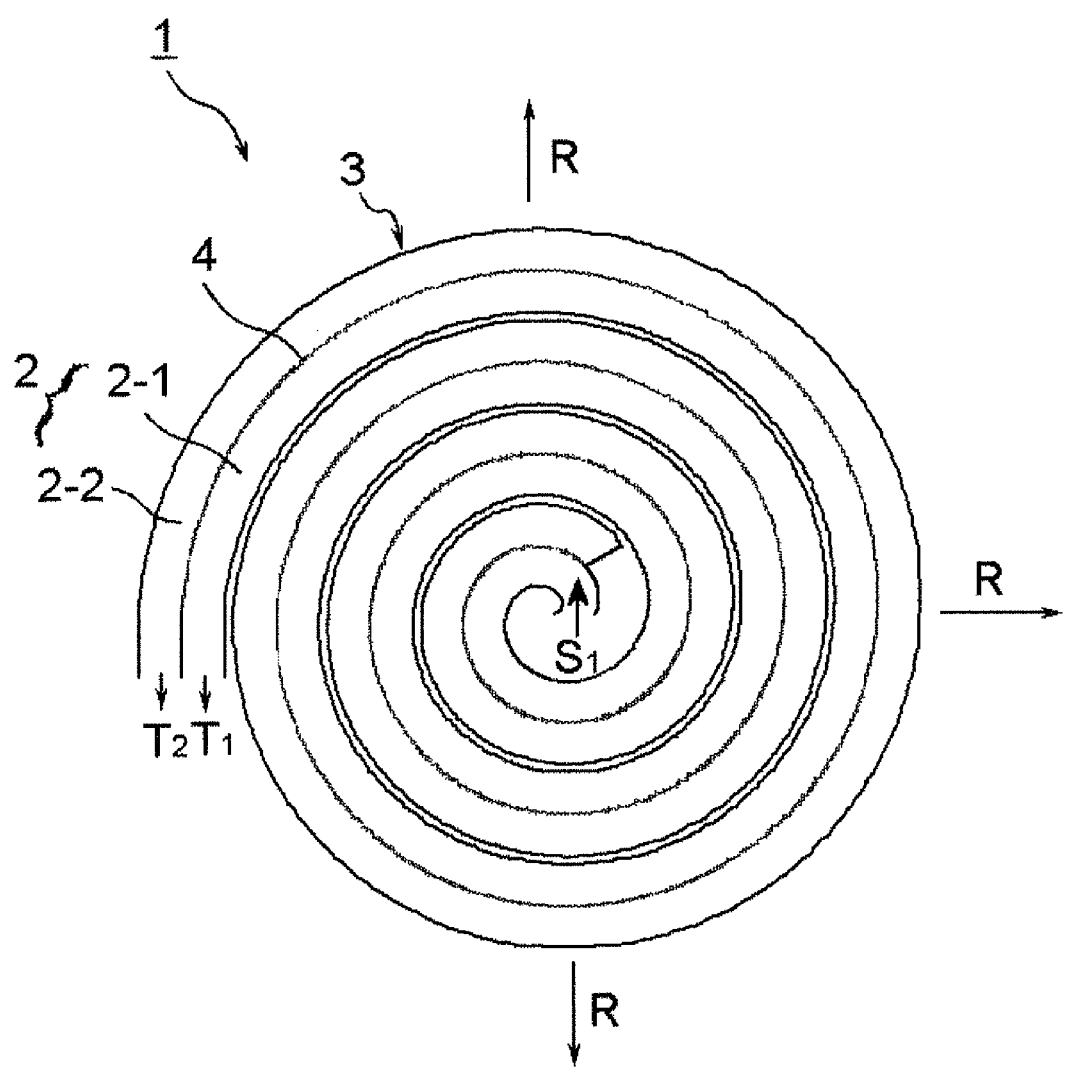
FIG. 17 is a plan view of the classifying device used in Example 3.
Figure 18:
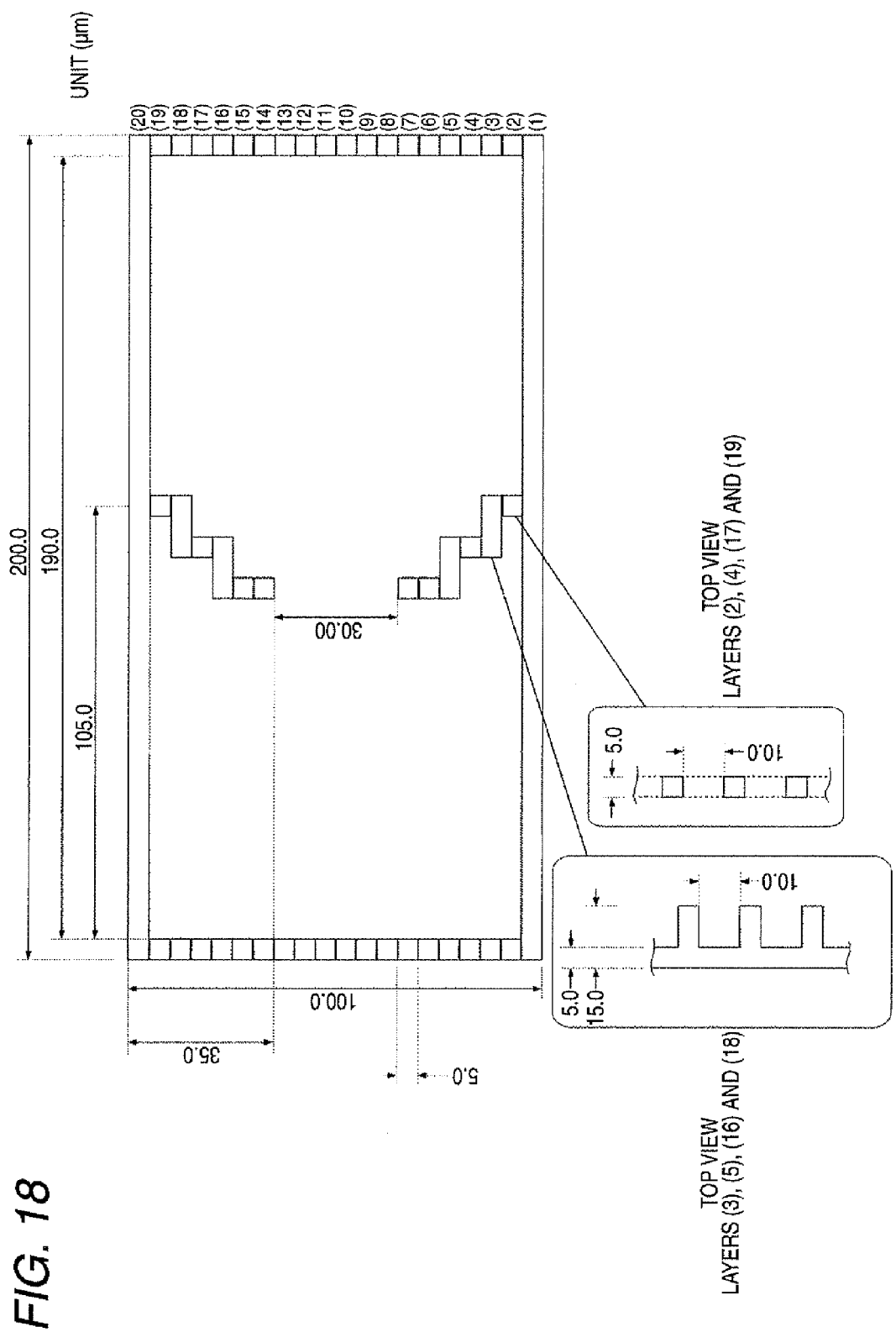
FIG. 18 is a diagram of the channel's profile section along the centrifugal force in the classifying device used in Example 3.

In FIG. 17, a plan view of the classifying device used in Example 3 is shown. Further, a diagram of the channel's profile section along the centrifugal force in the classifying device used in Example 3 is shown in FIG. 18. In the classifying device used in Example 3, a diaphragm sloping away from the channel's top face and bottom face in the direction of centrifugal force is formed, the mesh of apertured group located in the diaphragm's center region in the vertical direction is 30 μm, and the mesh of apertured group located near the top and bottom faces of the channel is 10 μm. In addition, as shown in FIG. 18, the diaphragm may be formed by lamination of 20 thin-layer patterns. Making an additional remark, two layers of apertured group with a mesh of 10 μm is formed in the vicinity of each of the top and bottom faces of the channel in the classifying device used in Example 3.

The microchannel of the classifying device shown in FIG. 17 has the shape of an Archimedean spiral. Characteristic values of the classifying device are shown in the following Table 3. Additionally, the channel satisfies the equation $r[\mu m] = 35\theta[rad] + 100 \ [\mu m]$.

TABLE 3

| | |
|---|---|
| Rectangular channel width [μm] | 190 |
| Rectangular channel height [μm] | 90 |
| Channel area [m$^2$] | $1.7 \times 10^{-8}$ |
| Flow rate [ml/min] | 5 |
| Flow velocity V [m/s] | 4.87 |
| Total channel length L [mm] | 4.1 |
| Solution density ρ [kg/m$^3$] | 1120 |
| Viscosity coefficient μ [Pa/s] | 0.035 |
| Equivalent hydraulic diameter (typical length) D [m] | $1.22 \times 10^{-4}$ |

The Dean number (average) of the classifying device in Example 3 is 39.2.

Figure 19:
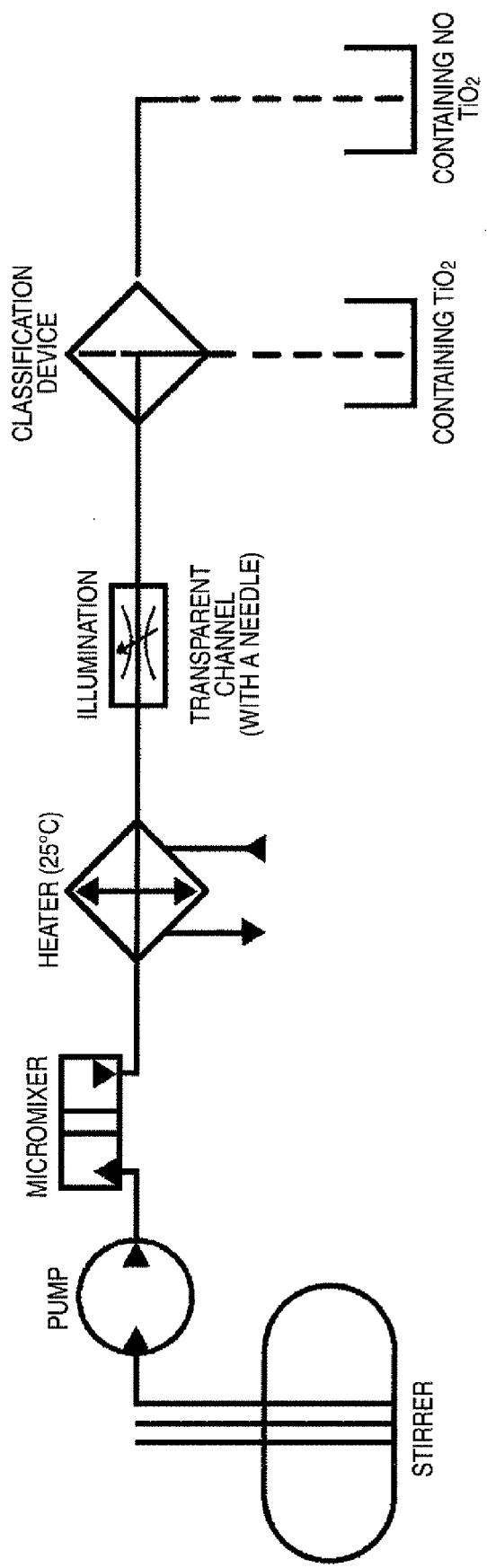
FIG. 19 is a block diagram of the overall apparatus used in Example 3.

Human blood containing influenza viruses is fed into the microchannel of the classifying device shown in FIG. 17 from a fill port situated at the end of the outermost course, and that on the inner side relative to the direction of centrifugal force. Incidentally, the entire apparatus used in this Example is configured as shown in FIG. 19.

Therein, $TiO_2$ photocatalyst is charged into human blood infected by malignant viruses, thereby deactivating the viruses, and at the same time, the catalyst particles are recovered.

More specifically, the blood sample and $TiO_2$ are thoroughly stirred, then fed into a micromixer by use of a pump, and mixed together by means of the micromixer. The resulting blood-$TiO_2$ mixture is sent forth while maintaining its temperature at 25° C. by use of a heater so as to retain the activity of fine $TiO_2$ particles and prevent coagulation of the blood. Then, the mixture is fed into a needle-attached transparent channel. Simultaneously with this feeding, the mixture is exposed to light from illumination (by a fluorescent lamp). By doing so, the fine $TiO_2$ particles exert their photocatalytic effect on viruses in the blood, and the viruses are deactivated.

In the next place, the resulting mixture is fed into the classifying device shown in FIG. 17 and separation of $TiO_2$ is performed.

In this Example, Sample $S_1$ containing blood and $TiO_2$ is fed into one of the channels formed by partitioning the microchannel with the diaphragm from a fill port situated at the end of the innermost course of the microchannel, and that on the inner side relative to the direction of centrifugal force. And discharged liquids ($T_1$ and $T_2$) are recovered from the outermost course of the microchannel, specifically from the channels on the inner and outer sides relative to the direction of centrifugal force, respectively.

In Comparative Example 3, on the other hand, classification is carried out in the same manner as in Example 3, except that no diaphragm is provided in the classifying device, and thereby discharged liquids $T_1$ and $T_2$ were recovered.

Figure 20:
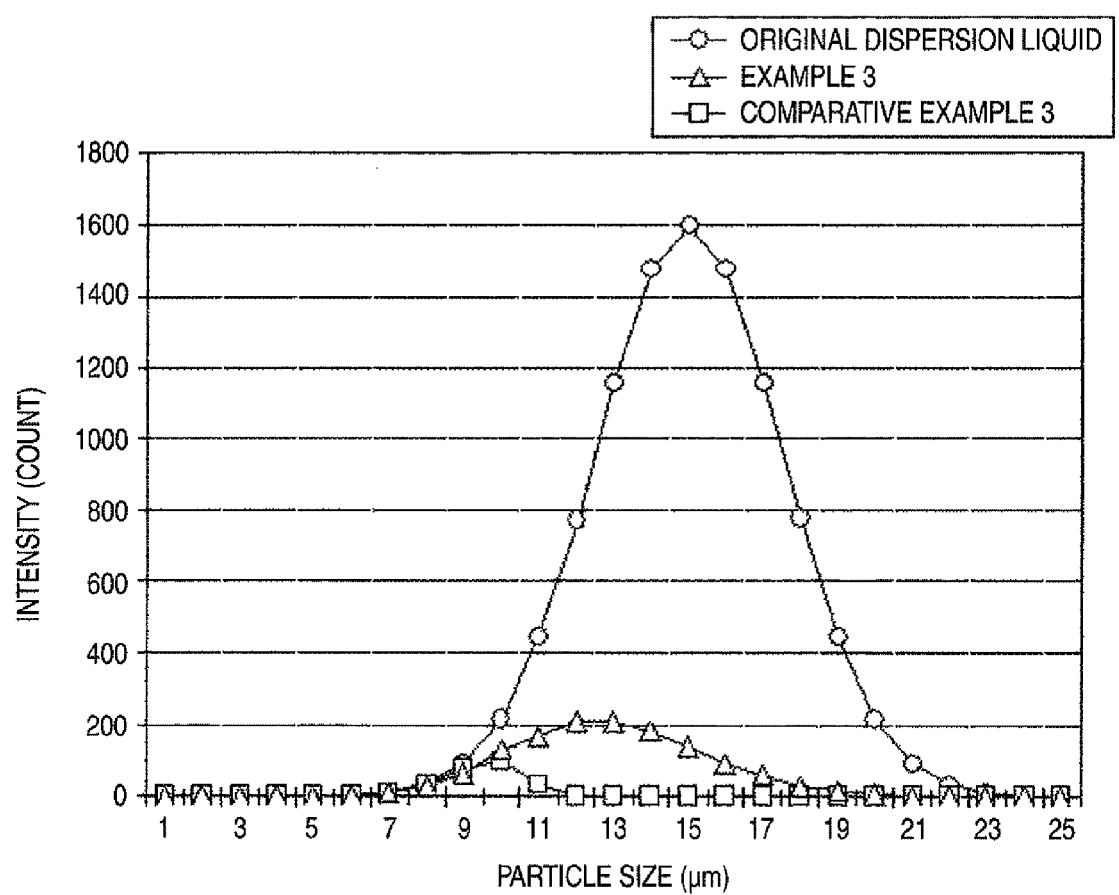
FIG. 20 shows results of measurements made on the dispersion state of particles in the original liquid fed into the classifying device and on the dispersion state of particles in the discharged liquid $T_2$ recovered from the outermost course of the microchannel situated on the outer side relative to the direction of centrifugal force in each of Example 3 and Comparative Example 3.

In FIG. 20 are shown results of measurements made on the dispersion state of particles in the original liquid fed into the classifying device and on the dispersion state of particles in the discharged liquid $T_2$ recovered from the outermost course of the microchannel situated on the outer side relative to the direction of centrifugal force in each of Example 3 and Comparative Example 3.

In addition, separation rates in Example 3 and Comparative Example 3 are shown in the following Table 4. Additionally, the term "separation rate" as used herein is defined as the percentage (%) by number of particles removed by classification.

TABLE 4

| | Separation Rate (%) |
|---|---|
| Example 3 | 90 |
| Comparative Example 3 | 78 |

The classifying device of Example 3 is high in separation rate as compared with the classifying device of Comparative Example 3, and the results shown in FIG. 20 indicate that the separation capability of the classifying device of Example 3 increased by a factor of 5.4.

As stated above, the classifying device as an exemplary embodiment of the invention is able to achieve high classification efficiency.

Furthermore, this device causes no clogging even when the operation thereof is continued for 12 hours, and allow continuous processing.

The foregoing description of the embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention defined by the following claims and their equivalents.

What is claimed is:

1. A classifying device for classifying particles using a centrifugal force, the classifying device comprising:
   a microchannel that includes a curved portion including a first tubular channel and a second tubular channel; and
   a diaphragm that is provided within the curved portion, and that is located at a position between the first tubular channel and the second tubular channel; and
   wherein
   the diaphragm has at least a first apertured group formed in a central region of the diaphragm and a second apertured group formed in a first end region and a second end region of the diaphragm, the central region being sandwiched between the first end region and the second end region,
   the first apertured group and the second apertured group communicate the first tubular channel with the second tubular channel along a direction of the centrifugal force,
   the first apertured group has a mesh, and
   the second apertured group has a mesh that is different in size from the mesh of the first apertured group.

2. The classifying device according to claim 1,
   wherein the mesh of the first apertured group defines an upper limit of particles to be classified and the mesh of the second apertured group defines a lower limit of particles to be classified.

3. The classifying device according to claim 1,
   wherein the first end region and the second end region of the diaphragm incline toward the direction of the centrifugal force so as to have a predetermined gradient.

4. The classifying device according to claim 1,
   wherein the first tubular channel locates outward relative to the direction of the centrifugal force across an entire length of the curved portion, and the second tubular channel locates inward relative to the direction of the centrifugal force across the entire length of the curved portion.

5. The classifying device according to claim 1,
   wherein the mesh of the first apertured group is bigger than the mesh of the second apertured group.

6. The classifying device according to claim 1,
   wherein the mesh of the first apertured group is smaller than the mesh of the second apertured group.

7. The classifying device according to claim 1,
   wherein the second apertured group includes two sub apertured groups, one sub apertured group being formed in the first end region of the diaphragm and the other sub apertured group being formed in the second end region of the diaphragm, and
   each of the two sub apertured groups has a mesh, meshes of the two sub apertured groups being same size.

8. The classifying device according to claim 1,
   wherein the second apertured group includes two sub apertured groups, one sub apertured group being formed in the first end region of the diaphragm and the other sub apertured group being formed in the second end region of the diaphragm, and
   a distance from a longitudinal edge of the diaphragm being close to the first end region to one sub apertured group formed in the first end region is approximately same as a distance from a longitudinal edge of the diaphragm being close to the second end region to the other sub apertured group formed in the second end region.

9. The classifying device according to claim 3,
   wherein the gradient of the first end region and second end region of the diaphragm is more than about 0° but not over about 60°.

10. The classifying device according to claim 1, wherein a particles-dispersed liquid flows into a first tubular channel of a classifying device to classify particles using a centrifugal force.

11. The classifying device according to claim 10,
    wherein the particle dispersed liquid flows to achieve a dean number of about 8 or higher in the curved portion.

12. The classifying device according to claim 10,
    wherein the mesh of the first apertured group defines an upper limit of particles to be classified and the mesh of the second apertured group defines a lower limit of particles to be classified.

13. The classifying device according to claim 10,
    wherein the first end region and the second end region of the diaphragm incline toward the direction of the centrifugal force so as to have a predetermined gradient.

14. The classifying device according to claim 10,
    wherein the first tubular channel locates outward relative to the direction of the centrifugal force across an entire length of the curved portion, and the second tubular channel locates inward relative to the direction of the centrifugal force across the entire length of the curved portion.

15. The classifying device according to claim 10,
    wherein the mesh of the first apertured group is bigger than the mesh of the second apertured group.

16. The classifying device according to claim 10,
    wherein the mesh of the first apertured group is smaller than the mesh of the second apertured group.

17. The classifying device according to claim 10,
    wherein the second apertured group includes two sub apertured groups, one sub apertured group being formed in the first end region of the diaphragm and the other sub apertured group being formed in the second end region of the diaphragm, and
    each of the two sub apertured groups has a mesh, meshes of the two sub apertured groups being same size.

18. The classifying device according to claim 10,
    wherein the second apertured group includes two sub apertured groups, one sub apertured group being formed in the first end region of the diaphragm and the other sub apertured group being formed in the second end region of the diaphragm, and
    a distance from a longitudinal edge of the diaphragm being close to the first end region to one sub apertured group formed in the first end region is approximately same as a distance from a longitudinal edge of the diaphragm being close to the second end region to the other sub apertured group formed in the second end region.

19. The classifying device according to claim 13,
    wherein the gradient of the first end region and second end region of the diaphragm is more than about 0° but not over about 60°.

* * * * *